(12) United States Patent
Jones et al.

(10) Patent No.: US 7,871,425 B2
(45) Date of Patent: Jan. 18, 2011

(54) MINIMALLY-INVASIVE NIPPLE-LIFT PROCEDURE AND APPARATUS

(75) Inventors: Richard G. Jones, West Chester, PA (US); Benjamin Schlechter, Wyomissing, PA (US)

(73) Assignee: Angiotech Pharmaceuticals, Inc. (CA)

( * ) Notice: Subject to any disclaimer, the term of this patent is extended or adjusted under 35 U.S.C. 154(b) by 607 days.

(21) Appl. No.: 11/829,550

(22) Filed: Jul. 27, 2007

(65) Prior Publication Data

US 2008/0027486 A1 Jan. 31, 2008

Related U.S. Application Data

(60) Provisional application No. 60/833,999, filed on Jul. 28, 2006.

(51) Int. Cl.
*A61B 17/06* (2006.01)
(52) U.S. Cl. ..................... 606/224; 606/228
(58) Field of Classification Search ............. 606/139, 606/144–150, 215–217, 222–233; 128/898; 623/7, 8, 23.72; 604/7, 8
See application file for complete search history.

(56) References Cited

U.S. PATENT DOCUMENTS

| 5,658,328 | A | * | 8/1997 | Johnson | 623/8 |
| 5,676,161 | A | * | 10/1997 | Breiner | 128/898 |
| 7,056,331 | B2 | * | 6/2006 | Kaplan et al. | 606/228 |
| 2005/0267531 | A1 | * | 12/2005 | Ruff et al. | 606/228 |
| 2006/0167338 | A1 | * | 7/2006 | Shfaram | 600/37 |
| 2008/0027273 | A1 | * | 1/2008 | Gutterman | 600/37 |

FOREIGN PATENT DOCUMENTS

| WO | WO 2004/112853 | 12/2004 |
| WO | WO 2005/096956 | 10/2005 |

OTHER PUBLICATIONS

International Search Report for PCT/US2007/074658 dated Jun. 12, 2007, 13 pages.

* cited by examiner

*Primary Examiner*—Melanie Tyson
(74) *Attorney, Agent, or Firm*—Angiotech

(57) ABSTRACT

Medical devices and methods are provided for a minimally-invasive mastoplasty procedure. In the procedure, barbed sutures are used to accomplish a nipple-lift by deploying the sutures cranially from the nipple-areolar complex to stable anatomical features higher on the chest. Additional barbed sutures may be used to accomplish a breast-lift and/or breast contouring by deploying the sutures caudally from stable anatomical features into the breast tissue.

20 Claims, 21 Drawing Sheets

MINIMALLY-INVASIVE NIPPLE-LIFT PROCEDURE AND APPARATUS

CLAIM OF PRIORITY

This application claims priority to U.S. Provisional Application No. 60/833,999 entitled "Minimally-Invasive Mastoplasty Procedure" filed Jul. 28, 2006 and which is hereby incorporated by reference.

BACKGROUND OF INVENTION

This invention relates to minimally-invasive methods and medical devices for performing cosmetic breast surgery or mastoplasty. More, specifically, the invention provides methods and devices for performing breast and nipple-lifts and contouring the surface of the breast without the need for open surgery.

A breast-lift (mastopexy) is usually performed for drooping breasts (mastoptosis), which may occur with age, after weight-loss or after a woman has had children. The skin loses its elasticity and the breasts lose their firmness and shape as they sag under the effects of gravity. The degree of droop or ptosis is measured by how far the nipple has fallen below the inframammary fold. Mastoptosis requiring mastopexy is present when the nipple has fallen below the plane of the projected inframammary fold. However, cosmetic breast surgery or mastoplasty may be performed for aesthetic reasons regardless of the extent of ptosis present.

Surgical mastopexy is the standard treatment for mastoptosis. In 2004 more than 98,000 mastopexy procedures were performed in the United States. Breast-revision surgery such as mastopexy is an invasive open surgery procedure. The procedure is performed under general anesthesia, either in an outpatient facility or in the hospital. Most patients require a two-day hospital stay. During the procedure, incisions are made along the natural creases in the breast and around the dark pink skin surrounding the nipple (areolus). A keyhole-shaped incision above the areolus is made to define the new location of the nipple. Skin is then removed from the lower section of the breast. The areolus, nipple (nipple-areola complex or NAC), and underlying breast tissue are moved up to a higher position. The breasts are lifted using suspension sutures in the deep parenchymal tissue and tucks in the redundant skin. The NAC is moved up into the keyhole incision and all the incisions are closed with sutures. Large incisions are required, and in order to elevate the NAC, periareola incisions are always required. The sutures remain for two weeks after surgery and are then removed. It is a disadvantage of the mastopexy procedure that it requires long incisions, and, although care is taken to reduce scarring, some scarring is usually evident. A further disadvantage is that the long incisions and exposed tissues create a risk of post-operative infection.

After surgery, a bulky gauze dressing is wrapped around the breasts and chest. Sometimes a surgical bra is used. The patient is usually in significant pain, which necessitates control by medication for the first few days. Generally, the swelling and discoloration around the incisions take a few days to subside. The surgical dressing must be worn for up to a week at which point it is replaced with a surgical bra, which must be worn for several weeks.

Thus, the open mastopexy procedure requires a lengthy hospital stay and an even longer convalescence period in which the patient may not be able to work. Patients may not return to even low impact exercise until three weeks following surgery and to higher impact activities such as jogging, until six weeks following surgery. The patient may suffer discomfort in this period after the procedure, requiring further medication. Possible side effect of the procedure, include scarring and temporary loss of sensation in the breast skin and nipples.

It would therefore be desirable to provide a breast-lift and/or NAC-lift procedure, which does not require long incisions and can be performed with a minimally-invasive procedure.

It would also be desirable to provide a breast-lift and/or NAC-lift procedure, which reduces the pain, and discomfort suffered by the patient and reduces the recovery time of the patient.

It would further be desirable to provide a breast-lift and/or NAC-lift procedure, which reduces the risk of scarring and scar tissue formation.

It would still further be desirable to provide a breast-lift and/or NAC-lift procedure with reduced incidence of side effects such as temporary loss of sensation and infection.

BRIEF DESCRIPTION OF THE DRAWINGS

Features of the invention, its nature and various advantages will be apparent from the accompanying drawings and the following detailed description of various embodiments, in which.

DETAILED DESCRIPTION

Figure 1:
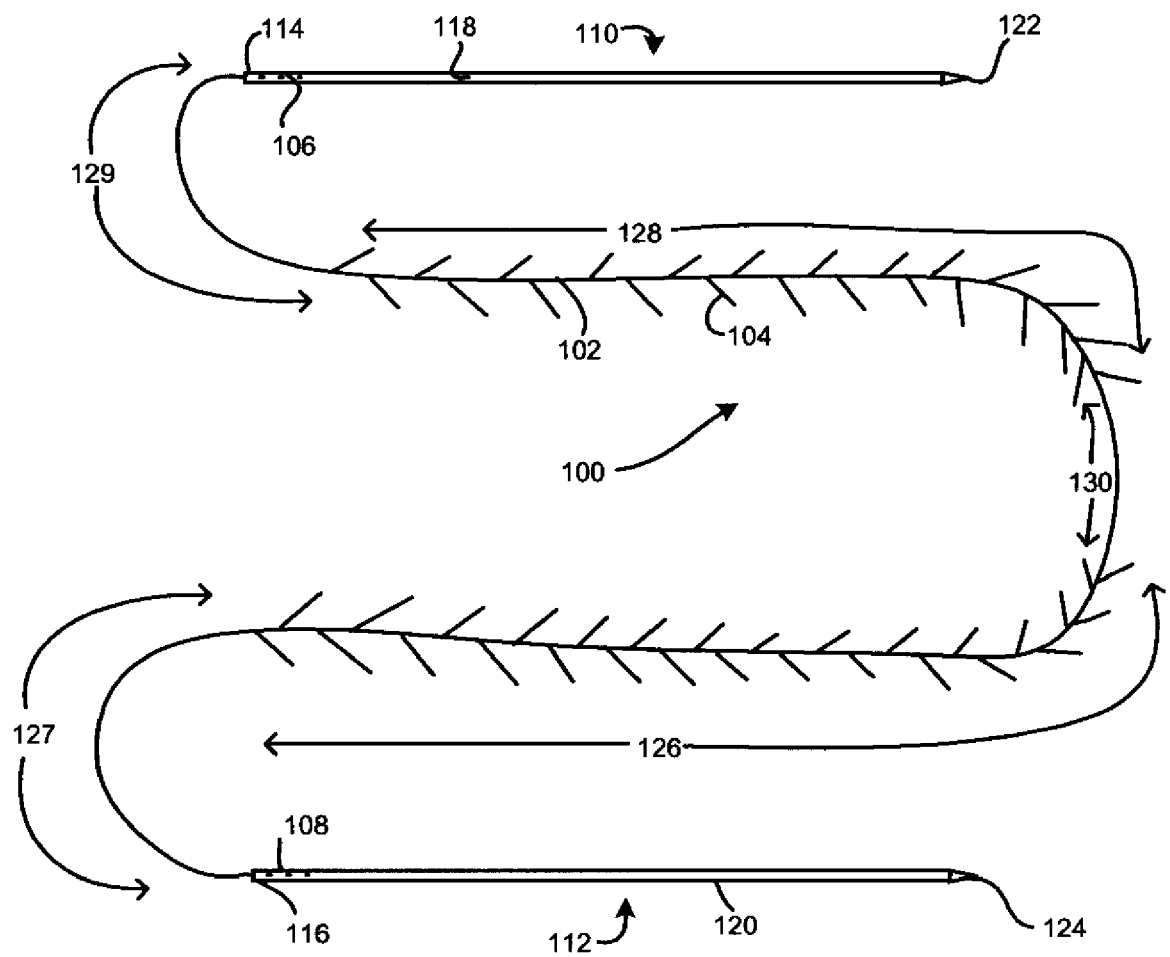
FIG. 1 shows a suture for performing procedures of an embodiment of the present invention.

In view of the foregoing background of the invention, it is an object of the present invention to provide a breast-lift procedure which does not require long incisions and can be performed with a minimally-invasive procedure.

It is also an object of the present invention to provide a breast-lift and NAC-lift procedure, which reduces the pain, and discomfort suffered by the patient and reduces the recovery time of the patient.

It is a further object of the present invention to provide a breast-lift and NAC-lift procedure, which reduces the risk of scarring and scar tissue formation.

It is a still further object of the present invention to provide a breast-lift and NAC-lift procedure with reduced incidence of side effects such as temporary loss of sensation and infection.

These and other objects of the present invention are accomplished as described in the drawings and detailed description of the invention by providing a minimally-invasive breast-lift and/or NAC-lift procedure that utilized one or more lengths of barbed suture material introduced through tiny punctures to lift and contour the breast and/or lift the NAC. The invention provides a range of procedures for deploying the bidirectional sutures depending upon the lifting and contouing effects desired to be achieved and the patient's anatomy.

In a general embodiment, one or more lengths of bidirectionally-barbed suture are introduced through puncture wounds above the breast and fixated to a stable anatomical feature such as the fascia pectoralis. Long needles are utilized to deploy both ends of the suture caudally from the insertion point through breast tissue to exit lower on the breast. The deployment lines and deployment depth are controlled to achieve the desired effects. When the sutures are in place, the breast tissues are manually advanced along the sutures until the desired elevation and contouring is achieved. The barbs on the sutures are oriented to optimally support the tissue against gravity along the length of the sutures and maintain the desired contouring and elevation. In this manner, the effects of surgical mastopoxy can be achieved without long incisions and the associated disadvantages of pain, scaring, and possible loss of sensation.

Other objects, advantages, and embodiments of the invention are set forth in part in the drawings, the description which follows, and in part, will be obvious from the drawings and the description, or may be learned from the practice of the invention.

Barbed Sutures

Referring now to the drawings, wherein like reference numerals designate corresponding or similar elements throughout the several views, there is shown in FIGS. 1, 2A, 2B and 2C a bidirectional barbed suture for use according to the present invention and generally designated at 100. Suture 100 includes an elongated body 102 having a plurality of barbs 104 disposed along the length of the body 102. First and second ends 106, 108 of body 102 are affixed to needles 110, 112 for penetrating tissue. Needles 110, 112 each have: a proximal end 114, 116 for receiving suture 100; an elongate shaft 118, 120; and a sharp distal tip 122, 124 for penetrating tissue in a controllable and steerable manner. Needles 110, 112 are shown as straight needles but they may be curved as necessitated by the demands of the procedure.

Body 102 of suture 100 is, in one embodiment, circular in cross section. Suitable diameters for body 102 of suture 100 may range from about 0.001 mm to about 1.0 mm. In general, body 102 of suture 100 should be sized such that it has sufficient tensile strength to serve in its intended application but does not cause unnecessary least disruption to the tissues through which it passes. Body 102 of suture 100 could also have a non-circular cross-sectional shape, which would increase the surface area of body 102 and facilitate the formation of multiple barbs 104.

The plurality of barbs 104 is axially spaced along body 102 of suture 100. Barbs 104 are oriented in one direction facing toward the first end 106 of the suture 100 for a first portion 128 of the length of the suture and in an opposite direction facing the second end 108 of the suture 100 for a second portion 126 of the suture. Optionally suture 100 may also be unbarbed in a third portion 129 located between barbed section 128 and needle 110, and fourth portion 127 located between barbed section 126 and needle 112. These additional portions of the suture need not be barbed as they will not remain in the patient after deployment but they are useful during deployment. These portions can be left unbarbed to make them stronger and easier to handle during the procedure.

Figure 2A:
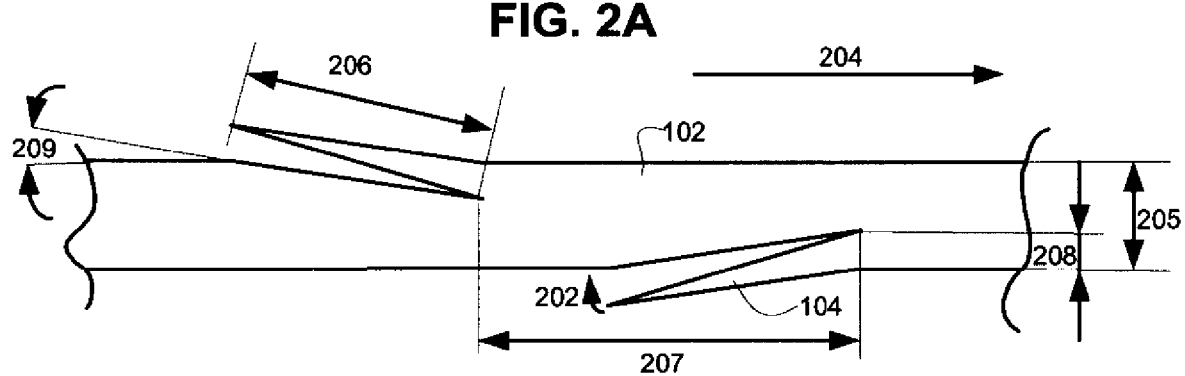
FIGS. 2A-2C show detail views of the suture of FIG. 1.

Barbs 104 are yieldable toward body 102 as shown by arrow 202 of FIG. 2A. Barbs 104 on each portion 126, 128 of suture 100 are oriented to allow movement of suture 100 through the tissue in one direction along with the corresponding end 106, 108 of suture 100. Arrow 204 of FIG. 2A indicates the direction in which body 102 may move through tissue. Barbs 104 are generally rigid in an opposite direction to prevent suture 100 from moving in the tissue in the opposite direction. Section 130 between sections 126,128 is unbarbed to increase its tensile strength. Suture 100 could be formed in one piece or could be formed from two sutures each with barbs oriented in one direction. Two sutures 100 could be tied or joined together at their ends.

Barbs 104 can be arranged in any suitable pattern, for example, in a helical pattern. The number, configuration, spacing and surface area of barbs 104 can vary depending upon the tissue in which suture 100 is used, and depending on the composition and geometry of the suture body. The proportions of barbs 104 may remain relatively constant while the overall length of barbs 104 and the spacing of barbs 104 are determined by the tissue being connected. If suture 100 is intended for use in fatty parenchymal tissue, which is relatively soft, barbs 104 can be made longer and spaced farther apart to increase the holding ability in the soft tissue. Moreover, the ratio of the number of barbs 104 on the first portion 126 of the suture 100 to the number of barbs 104 on the second portion 128, and the lengths of each portion 126, 128, 130 can vary depending on the application and needs. The length of suture 100 and sections 126, 127, 128, 129, 130 can vary depending on several factors such as variations in patient anatomy and the particular deployment pattern selected. A suture 100 of proper length is selected for achieving suitable results in a particular application.

The surface area of the barbs 104 can also vary. For example, fuller-tipped barbs 104 can be made of varying sizes designed for specific surgical applications. For joining fat and relatively soft tissues, larger barbs 104 are desired, whereas smaller barbs 104 are more suited for collagen-dense tissues. There are also situations where a combination of large and small barbs 104 within the same structure will be beneficial such as when a suture 100 is used in tissue repair with differing layer structures. Use of the combination of large and small barbs 104 with the same suture 100 wherein barb 104 sizes are customized for each tissue layer will ensure maximum anchoring properties.

Figure 2B:
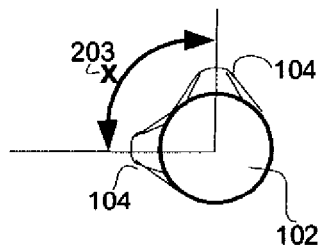

One method of creating barbed suture is to take a standard suture thread and cut barbs with a desired geometry. As shown in FIG. 2A, barbs 104 can be specified by a number of characteristics. Cut angle 209 defines the angle at which a blade enters the suture to cut the barb. Barb length 206 defines the length of the cut made into the suture at the cutting angle. Barb spacing 207 is the axial distance between adjacent barbs. Cut depth 208 is the maximum depth of the cut into the suture measured radially. The cut depth 208 is dependent upon the cut angle 209 and cut length 206. The cut depth needs to be chosen based on the diameter 205 of suture 100 such that suture 100 has enough tensile strength to perform the tasks for which it is intended. The barbs can be arranged in any suitable pattern on the suture. The barbs are shown in FIG. 2A on opposite sides of body 102 for ease of explanation. However, as shown in FIG. 2B, a cross-sectional view along the axis of body 102, the geometry of the barbs can be defined by the angle X between adjacent barbs 104. If the barbs are cut by a single blade, the suture material may be rotated between cuts, in which case, angle X is controlled by the number of times suture body 102 is rotated per unit distance.

Material for the body 102 of the suture 100 is available in a wide variety of monofilament suture material. The particular suture material chosen depends on the strength and flexibility requirements. In one embodiment, the material for body 102 is flexible and substantially nonresilient so that the shape of an inserted suture 100 will be determined by the line of insertion and the surrounding tissue. In some applications, however, it may be desirable for at least a portion of the body 102 to have sufficient dimensional stability to assume a substantially rigid configuration during use and sufficient resiliency to return to a predetermined position after deflection therefrom. Variations in surface texture of the body 102 of the suture 100 can impart different interaction characteristics with tissues.

Body 102 of suture 100 may be formed from non-absorbable material such as nylon, polyethylene terephthalate (polyester), polypropylene, and expanded polytetrafluoroethylene (ePTFE). Alternatively, suture body 102 can also be formed of metal (e.g. steel), metal alloys, plastic, or the like. It is also desirable that the material be of high tensile strength and low visibility. In one embodiment, the suture is formed from transparent polyester so as to reduce its visibility after implantation.

The needles may be constructed of stainless steel or other surgical grade metal alloy. The length of the needles is selected to serve the type of tissue being repaired so that the needles can be completely removed leaving the suture body 102 in the desired position within the tissue. In one embodiment of the present invention, the needles are 11-inch long straight needles with a taper tip having a cutting edge only on one side. An advantage of this type of tip is that it pushes away tissue at the tip rather than severing it as the needle passes. This reduces disruption to the tissues as the suture is deployed and reduces bruising and recovery time.

The needles may be secured to the suture body 102 by means of adhesives, crimping, swaging or the like, or the joint may be formed by heat shrinkable tubing. Alternatively the suture 100 may pass through an eye provided in the needle. A controlled-release connection may also be employed such that the needles may be removed from the body 102 of the suture 100 by a sharp tug or pull.

In one embodiment of a bidirectional suture for use in a breast-lift procedure such as shown in FIGS. 4A-4D, 5A-5L, 7A,B,D, the suture material is a clear, non-absorbable, sterile surgical strand of polypropylene of USP Size 2. Polypropylene is a suitable material for this application because polypropylene threads elicit a minimal acute inflammatory reaction in tissue. Implantation of polypropylene threads is followed by gradual encapsulation, however, polypropylene is not absorbed, and no known change in tensile strength in vivo has been identified.

In one embodiment for use in a breast-lift procedure, suture 100 is 111 cm long, barbed sections 126, 128 are each 19 cm long, unbarbed section 130 is 5 cm long and unbarbed sections 127, 129 are each 34 cm long. In another embodiment, suture 100 is 129 cm long, barbed sections 126, 128 are each 21.9 cm long, unbarbed section 130 is 5 cm long and unbarbed sections 127, 129 are each 40 cm long. The dimensions of the barbed section 126, 128 of suture 100 allow the suture to be deployed and support tissues along the entire length of the deployment paths required to perform the procedure. The additional unbarbed lengths 127, 129 of suture 100 allow insertion and withdrawal of the 11 inch needles during suture deployment but are not required to be barbed as they will not remain implanted in the patient.

In one embodiment for use in a breast-lift procedure, barbs 104 are cut into a standard USP size 2 polypropylene suture material with a circular cross-section. The barbs on barbed sections 126, 128 are defined as follows: cut angle 209 is 12 degrees; cut length 206 is 0.0320 inches; cut depth 208 is 0.0068"±0.0034 inches; and the distance 207 between barbs is 0.373 inches. The suture is rotated 2.21 times per inch of suture and there are approximately 27 barbs per inch, thus angle X between adjacent barbs is approximately 30 degrees. In one embodiment the minimum tensile strength of the suture after creation of barbs 104 is 8.0 lbs.

Figure 2C:
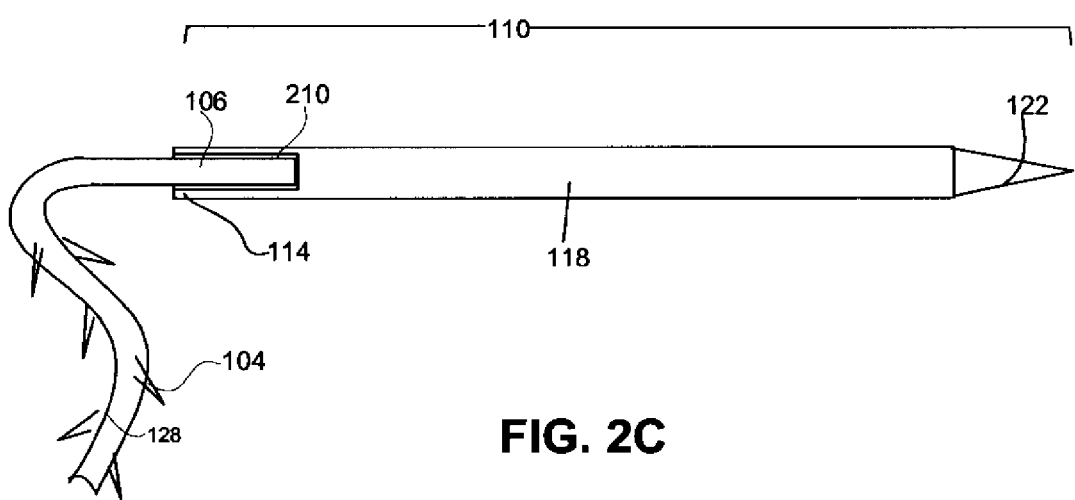

In one embodiment for use in a breast-lift procedure, the ends 106, 108 of suture 100 are swaged to the proximal ends 114, 116 of surgical needles 110, 112. For this embodiment, the needles are specified as: 470S/S, 0.039 inch diameter, 11 inches long with a taper cutting point. Needles 110, 112 are secured at each end of the body 102 of the suture 100 so that body 102 extends between the shank ends of the two needles (proximal ends 114, 116). As shown in FIG. 2C, needle 110 has an axial hole 210 at end 114 in which end 106 of suture 100 is swaged according to standard practice.

In one embodiment of a suture for an NAC-lift procedure in accordance with FIGS. 6A-6D, 7C,D the suture material is clear, non-absorbable, sterile surgical strand of polypropylene of USP Size 1-0. In one embodiment, suture 100 is 129 cm long, barbed sections 126, 128 are each 21.9 cm long, unbarbed section 130 is 5 cm long and unbarbed sections 127, 129 are each 40 cm long. The dimensions of the barbed section 126, 128 of suture 100 allow the suture to be deployed and support tissues along the entire length of the deployment paths required to perform the procedure. The additional unbarbed lengths 127, 129 of suture 100 allow insertion and withdrawal of the 11 inch needles during suture deployment but are not required to be barbed as they will not remain implanted in the patient.

In one embodiment of a suture for an NAC-lift procedure barbs 104 are cut into a standard USP size 1-0 polypropylene suture material with a circular cross-section. The barbs on barbed sections 126, 128 are cut into defined as follows: cut angle 209 is 12 degrees; cut length 206 is 0.0216 inches; cut depth 208 is 0.0046"±0.0023 inches; and the distance 207 between barbs is 0.373 inches. The suture is rotated 2.21 times per inch of suture and there are approximately 27 barbs per inch, thus angle X between adjacent barbs is approximately 30 degrees. In one embodiment the minimum tensile strength of the suture after creation of barbs 104 is 4.5 lbs.

In one embodiment of a suture for an NAC-lift procedure, the ends 106, 108 of suture 100 are swaged to the proximal ends 114, 116 of surgical needles 110, 112. For this embodiment, the needles are specified as: 470S/S, 0.039 inch diameter, 11 inches long with a taper cutting point. Needles 110, 112 are secured at each end of the body 102 of the suture 100 so that body 102 extends between the shank ends of the two needles (proximal ends 114, 116). As shown in FIG. 2C, needle 110 has an axial hole 210 at end 114 in which end 106 of suture 100 is swaged according to standard practice.

Surgical Procedures

The present invention provides a surgical procedure that uses one or more barbed sutures 100 to perform a minimally-invasive breast-lift or NAC-lift. In general, the procedure comprises the following steps: placement, fixation, deployment and elevation. Additionally, after the elevation step, any puncture wounds or incisions can be closed in standard surgical fashion. In the placement step, the physician locates and marks on the skin of the patient the insertion and exit points for the sutures, and the deployment lines along which the sutures will travel. The deployment lines are selected so that the suture, when deployed, engages the area of tissue required to be repositioned to achieve the desired effects. In the fixation step, the surgeon fixes the suture to a stable anatomical feature such as the fascia pectoralis to prevent movement or migration of an anchored portion of the suture and creates a fixation point or anchor. In the deployment step, the physician inserts the suture in a generally caudal or caudal and lateral direction along deployment lines between the insertion points and the exit points at a deployment depth selected based upon the type of tissues required to be engaged to achieve the desired effect. In the elevation step the physician applies tension to the free ends of the suture and manually groups and advances the tissues along the suture to achieve the desired elevation and contouring of the breast tissue. The barbs on the suture are oriented in such a way that the barbs along the length of the suture support the tissues in the elevated position. In the closing step, the physician removes the needles used during deployment, cuts off the excess suture material and closes the insertion and exit wounds.

After surgery, the patient is provided with appropriate postoperative care in accordance with standard post-operative practice. Subjects may be provided with breast support during recovery from the procedure. Breast support may include tape applied to the breast. For example, two pieces of two inch tape may be applied to the chest horizontally, medially and laterally with the tape touching at each corner of the lower pole of the breast. This creates a supportive "U" shape around/on the breast. Additionally, breast support may be provided in the form of a support bra.

As described above, in the fixation step, the surgeon fixes the suture to a stable anatomical feature to prevent movement of an anchored portion of the suture and creates a fixation point. One way to anchor the suture and create a fixation point is to loop the suture through the fascia pectoralis. The fascia pectoralis is a thin inelastic lamina of connective tissue, covering the surface of the muscles of the chest (pectoralis major). The fascia pectoralis is attached, in the middle line, to the front of the sternum; and above, to the clavicle. The fascia pectoralis is a stable anatomical feature that provides a strong and immobile anchor for the suture and thus prevents migration of the suture. The stability of the fascia pectoralis as an anchor is enhanced in regions proximate to the sternum and clavicle where the fascia pectoralis is connected to a bone.

Figure 3:
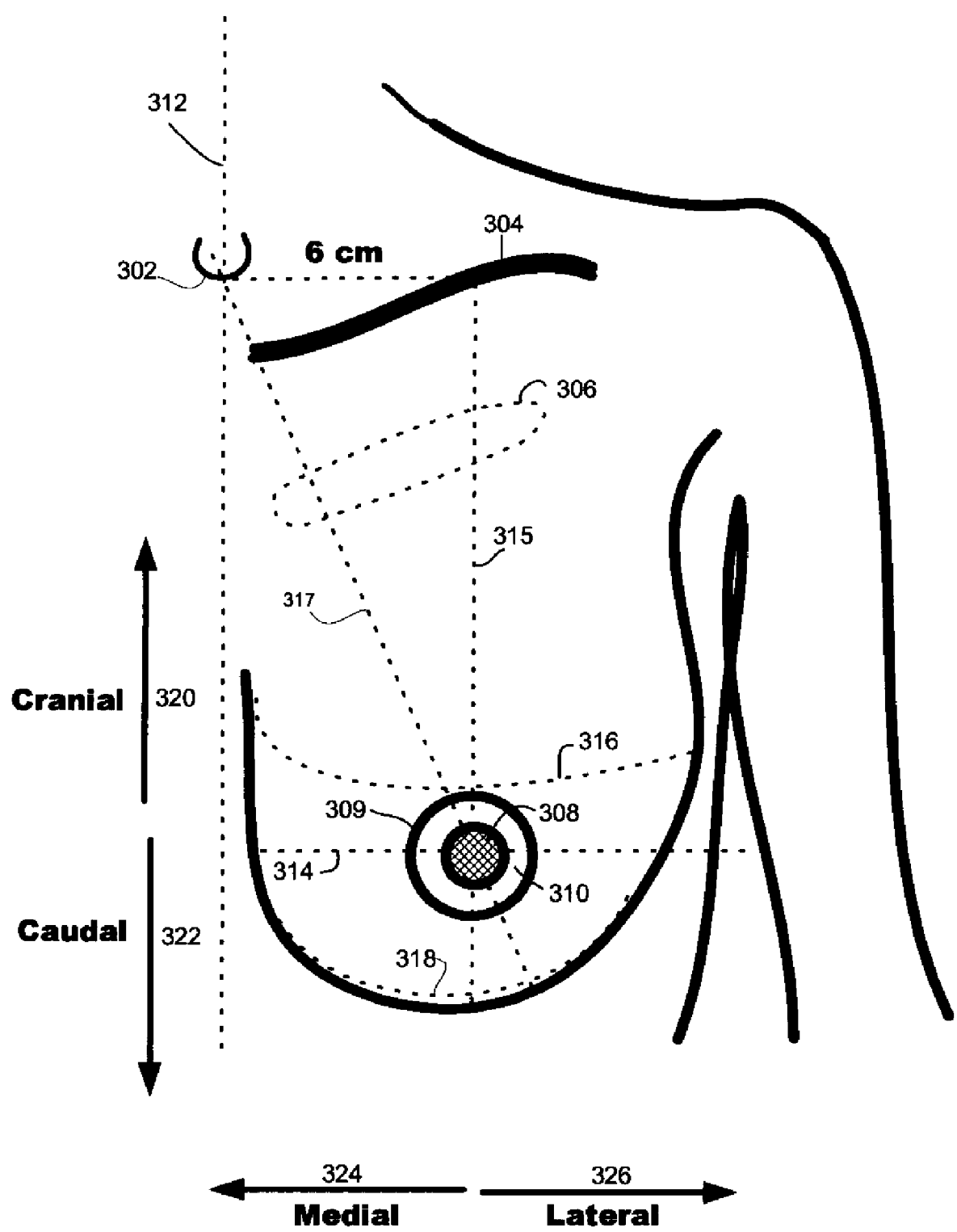
FIG. 3 shows anatomical features and markings that may be made during planning for a breast-lift and/or NAC-lift procedure.

FIG. 3 illustrates preparation the physician may make prior to placement of the sutures. During preparation for the procedure, the physician identifies particular anatomical features on the patient and marks navigational lines in ink on the patient to aid with the procedure. For example, the physician may identify, and mark if needed, the following anatomical reference points: sternal notch 302, clavicle 304, outline of second rib 306, nipple 308, areolus 310, midline 312, transethial line through the center of the nipple 314, natural breast vector 317 from the nipple through the sternal notch, inframammary fold 316, vertical line 315 and lowest contour line 318. Vertical line 315 is shown passing from the nipple to a position 6cm along the inferior border of the clavicle. Lowest contour line 318 is marked on the most pendent edge of the breast with the patient in an upright position. Navigation lines 314, 315, 317, and 318 are useful guides for determining the location of insertion and exit points and the appropriate trajectories for deployment of the sutures. The navigational lines are shown as dotted lines in FIG. 3 in order to avoid confusion with the anatomical features of the chest, however, a surgeon usually marks solid lines in ink on the patient during preparation for the procedure. Also shown in FIG. 3 are the relative directions: cranial 320 meaning towards the head; caudal 322 meaning toward the posterior; medial 324 meaning close to the midline; and lateral 326 meaning away from the midline. Other descriptors of direction may be used in this application as may be inferred from the context, for example, above, and higher may refer to a more cranial location, while below, lower and lowest may refer to a more caudal direction.

After identifying the anatomical markers of the patient, the physician may prepare for placement of the suture. As shown in the example breast-lift procedure of FIG. 4A, the physician marks insertion points 402, insertion-exit point 404, and exit points 406, 408 on the patient's skin using a marker. In one embodiment, points 402 and 404 are marked over the second rib one centimeter either side of natural breast vector 317 from the sternal notch to the nipple. As will be illustrated later, insertion-exit point 404 serves both as an exit point and an insertion point. In addition to the insertion and exit points, the physician also marks the intended trajectory of the suture on the patient's skin as indicated by dashed lines 410, 412, 414. Placement depends on the anatomy of the patient and the aesthetic effects desired by the patient. In general, for a breast-lift, the insertion points are above or cranial to the exit points on the breast. Depending on the anatomy, the insertion points may also be placed medial of the exit points as shown if FIG. 4A. In addition, the insertion points are located so as to allow anchoring of the suture to a stable anatomical feature such as the fascia pectoralis or the periosteum of a bone such as the clavicle, a rib or the sternum.

Figure 4A:
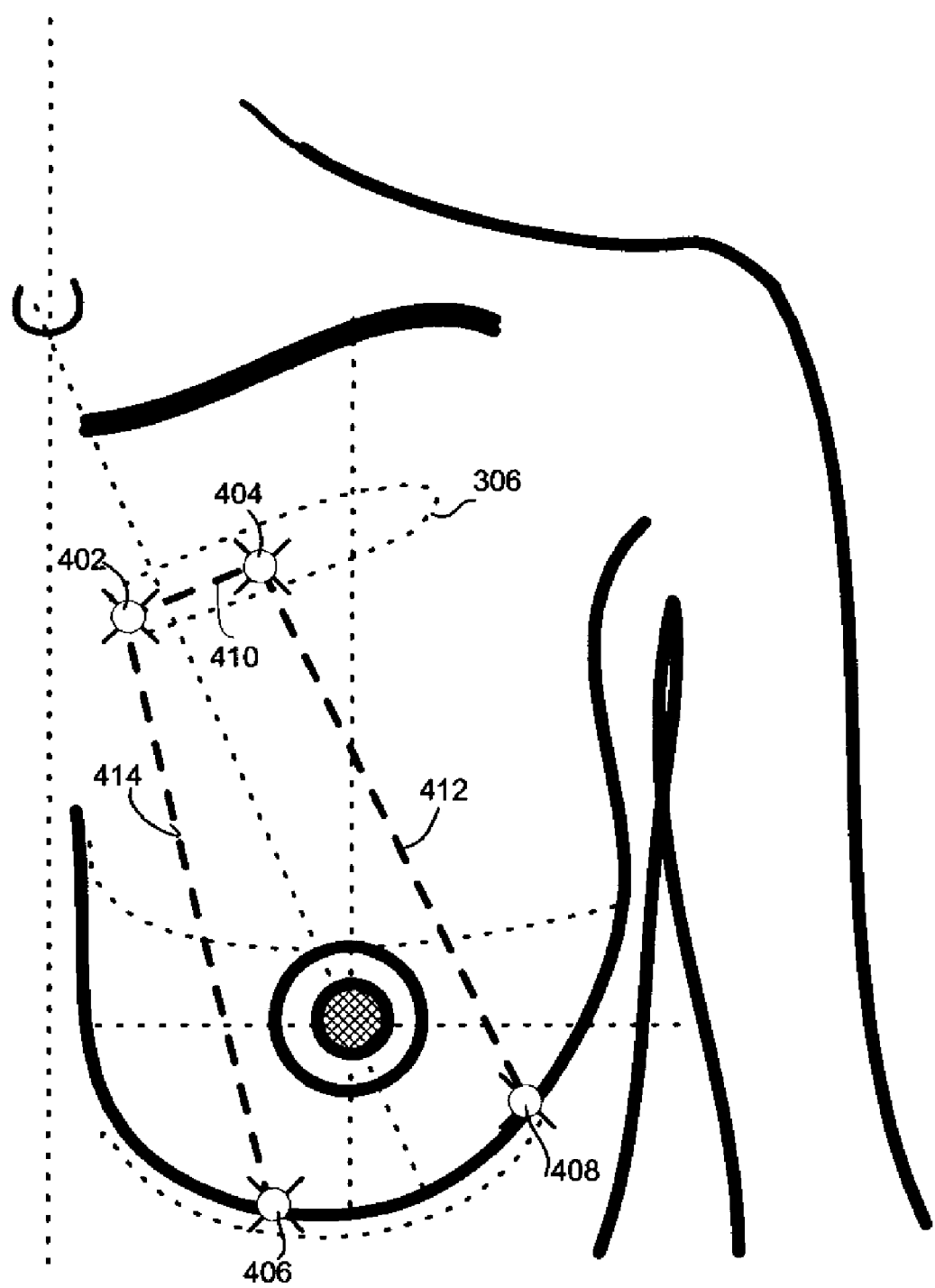
FIGS. 4A-D show the steps of a method for a breast-lift and/or NAC-lift procedure according to one embodiment of the present invention.

As shown in FIG. 4A insertion points 402, 404 are located over the outline of second rib 306. The location of the insertion points over the second rib reduces the risk of injury to the patient by perforation of the pleural membrane or by damage to the perforators of the breast. As shown in the embodiment of FIG. 4A, the long deployment lines 412, 414 pass in a generally caudal and lateral direction from the insertion points 402 404 to the exit points 406, 408. The shorter deployment line 410 is approximately horizontal along second rib 306 providing a stable anchor point. Fixation to the fascia pectoralis may be achieved along a deployment line between an insertion and exit point or may be achieved at a single site by looping through the fascia pectoralis at that site. Fixation point or anchor as used herein should not be limited to a single point but should encompass all appropriate methods of fixating the suture to the selected stable anatomical feature. By way of example, fixation of the suture to a stable anatomical feature, to create affixation point or anchor, could be achieved using an anchoring device placed in the tissue to which the suture is attached.

Prior to deployment of the sutures, the patient should be anaesthetized or sedated. In an open mastopexy procedure, a general anesthesia with its concomitant risks is always required. For the minimally-invasive procedure of the present invention, some patients may only require local anesthesia. Infiltration of local anesthetic along the deployment lines may be accomplished using a long small bore needle. The patient may be sedated if necessary. Some patients may still require general anesthesia to tolerate the procedure, but a significant number will not.

Figure 4B:
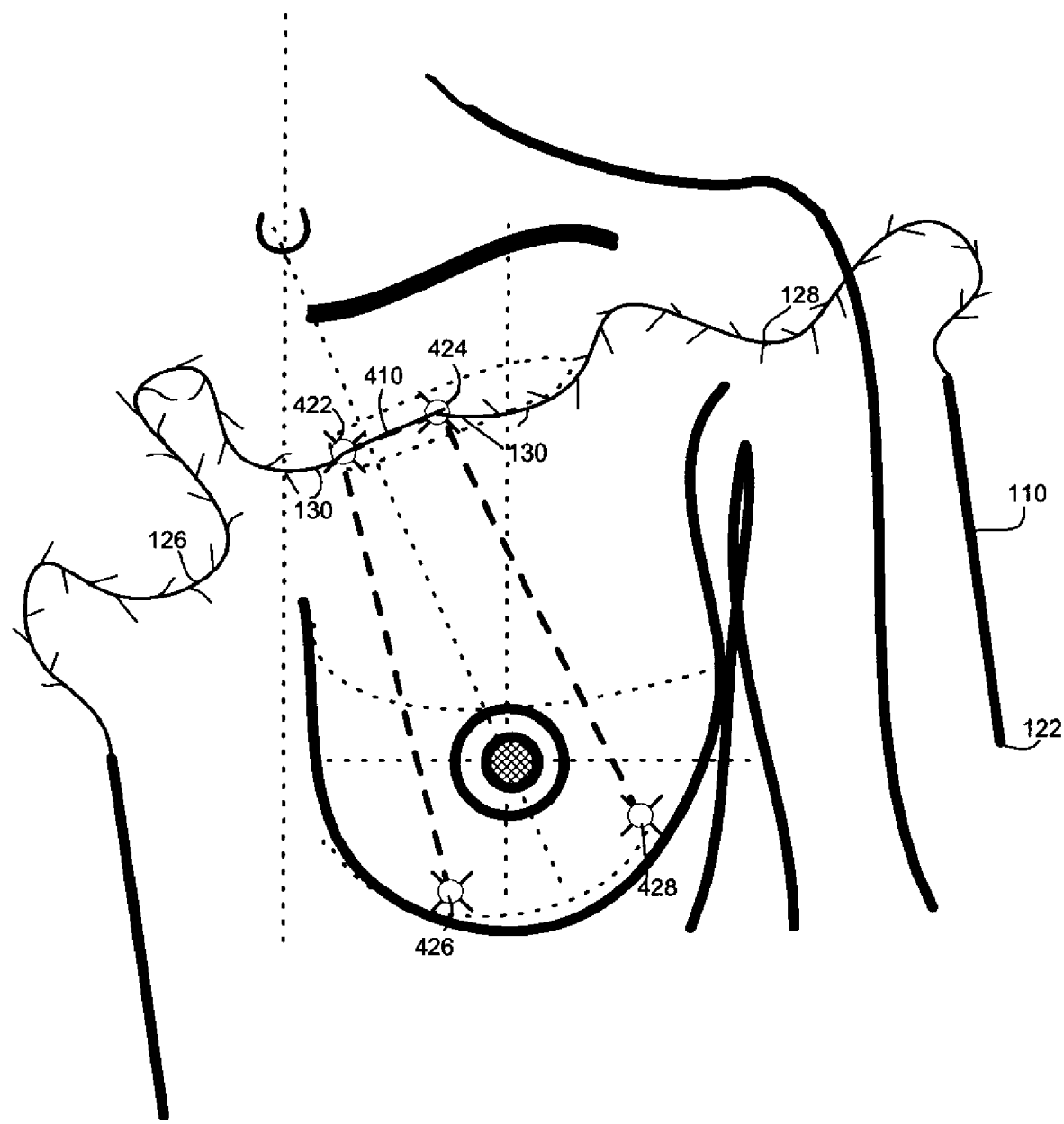

FIG. 4B illustrates the fixation step. As shown in FIG. 4B, the physician makes a puncture wound 422, 424, 426, 428 at each of the previously marked insertion and exit points 402, 404, 406, 408 respectively. One advantage of a puncture or stab wound is that the wound is more likely to close and heal without stitches or scarring. The creation of the puncture wound at the insertion points allows the surgeon to more safely penetrate the required tissues without excessive force. If the skin has already been punctured using a skin puncture device, when the physician introduces the needle he may better judge the depth of the needle and the force required to enter the selected tissues. However, the needles may be introduced and exit through the skin without the prior creation of puncture wounds if the surgeon is experienced with the techniques required.

After creation of the puncture wounds, if required, the physician inserts tip 122 of needle 110 into puncture wound 422 deep enough to penetrate the fascia pectoralis and directs tip 122 of needle 110 through the fascia pectoralis along deployment line 410 towards puncture wound 424. When tip 122 of needle 110 exits the fascia pectoralis through puncture wound 424 the physician takes hold of tip 122 and draws needle 110 and section 128 of suture 100 through the fascia pectoralis until section 130 of suture 100 lies between puncture wounds 422, 424 along deployment line 410 with a little of section 130 protruding from each puncture wound. Section 126 of suture 100 is not drawn into puncture wound 422, as the barbs on section 126 would obstruct motion through the tissue in that direction. Obviously, puncture wound 424 could be used as the insertion point and puncture wound 422 as the insertion-exit point to achieve the same result. The particular order in which the deployment is made is generally not important so long as the desired deployment pattern and orientation of the sutures can be achieved. After the fixation step, suture 100 is in the position shown in FIG. 4B. Section 130 of suture 100 is anchored in the fascia pectoralis over the second rib.

In an alternative method of introducing suture 100, a 14-gauge angiocatheter is inserted from insertion point 402 to insertion-exit point 404 through the fascia pectoralis along deployment line 410. The needle is then inserted into the catheter in a retrograde fashion along deployment line 410 from insertion point 422 to exit point 424. The catheter is removed when the tip of the needle has exited insertion-exit point 404 and the procedure continued in the same manner described above. Advantages of using an angio-catheter are that it can be used to safely make the punctures for introduction of the needle, and can reduce the risk of injury to the patient from the tip of the needle.

Figure 4C:
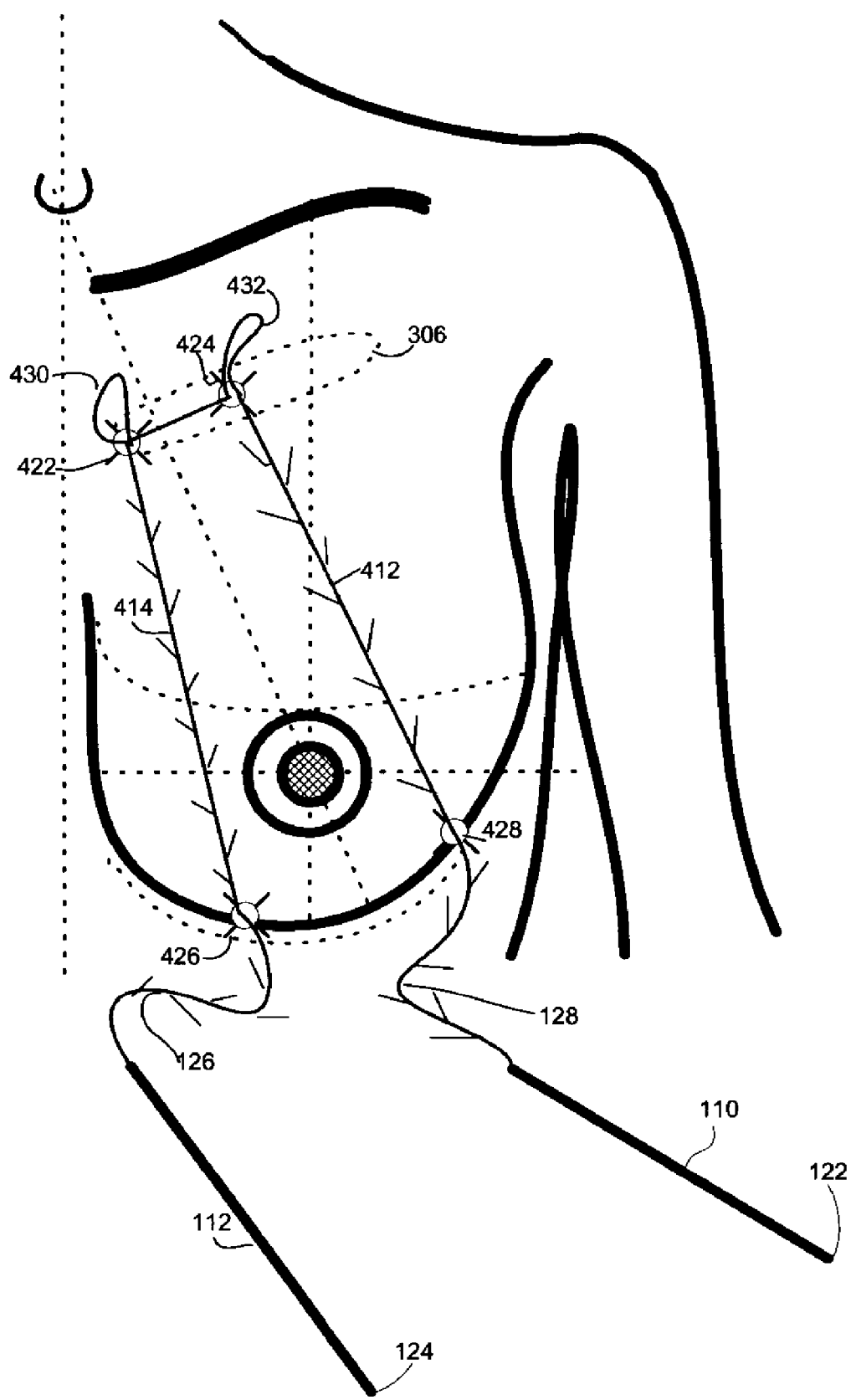

FIG. 4C illustrates the deployment step in which the physician deploys suture 100 along the deployment lines 412, 414. The physician first inserts tip 122 of needle 110 into puncture wound 424 and directs tip 122 of needle 110 through the breast tissue along deployment line 412 towards puncture wound 428. Note that, in this example, puncture wound 424 serves both as an insertion point and as an exit point for suture 100. During deployment, the physician may palpate the skin while introducing needle 110 to ensure that needle 110 passes at the correct depth in the tissue along deployment line 412.

The deployment depth determines the type of tissues to be engaged by the suture. If the desire is to lift the breast as a whole, the depth of deployment should be through deeper fatty and fibrous parenchymal tissues of the breast gland. If however, it is desired to selectively position or contour surface features of the breast, such as the skin of the breast and the nipple-areola complex (NAC), the deployment may be along a shallower subcutaneous line. The location of the deployment lines determines the area of tissues to be engaged by a suture. The combination of the location of the deployment lines and the depth of suture deployment will determine the type of tissues engaged and the aesthetic effects that elevation of the tissue along the suture will achieve.

Referring again to FIG. 4C, when tip 122 of needle 110 exits through puncture wound 428 the physician takes hold of tip 122 and draws needle 110 and section 128 of suture 100 through the tissue. The physician then repeats this process inserting tip 124 of needle 112 through puncture wound 422 along deployment line 414 and out through puncture wound 426. As shown in FIG. 4C, as suture 100 is drawn into the tissue, loops 430 and 432 of suture 100 remain external to puncture wounds 422, 424 until suture 100 is pulled tight. When the suture is pulled tight, section 130 of suture 100 is anchored in the fascia pectoralis over the second rib 306, section 128 of suture 100 has been deployed in the tissue of the patient between puncture wounds 424 and 428 along deployment line 412 and section 126 of suture 100 has been deployed in the tissue of the patient between puncture wounds 422 and 426 along deployment line 414. At this point, the needles are no longer required and may be removed from the suture.

Depending on the aesthetic effects desired, a physician may choose to deploy multiple sutures in the manner described above. For example, a physician may deploy one suture through deep breast structures and another suture along a shallower subcutaneous line. In this way, control of both elevation of the breast gland and elevation and contouring of the breast surface may be achieved.

Figure 4D:
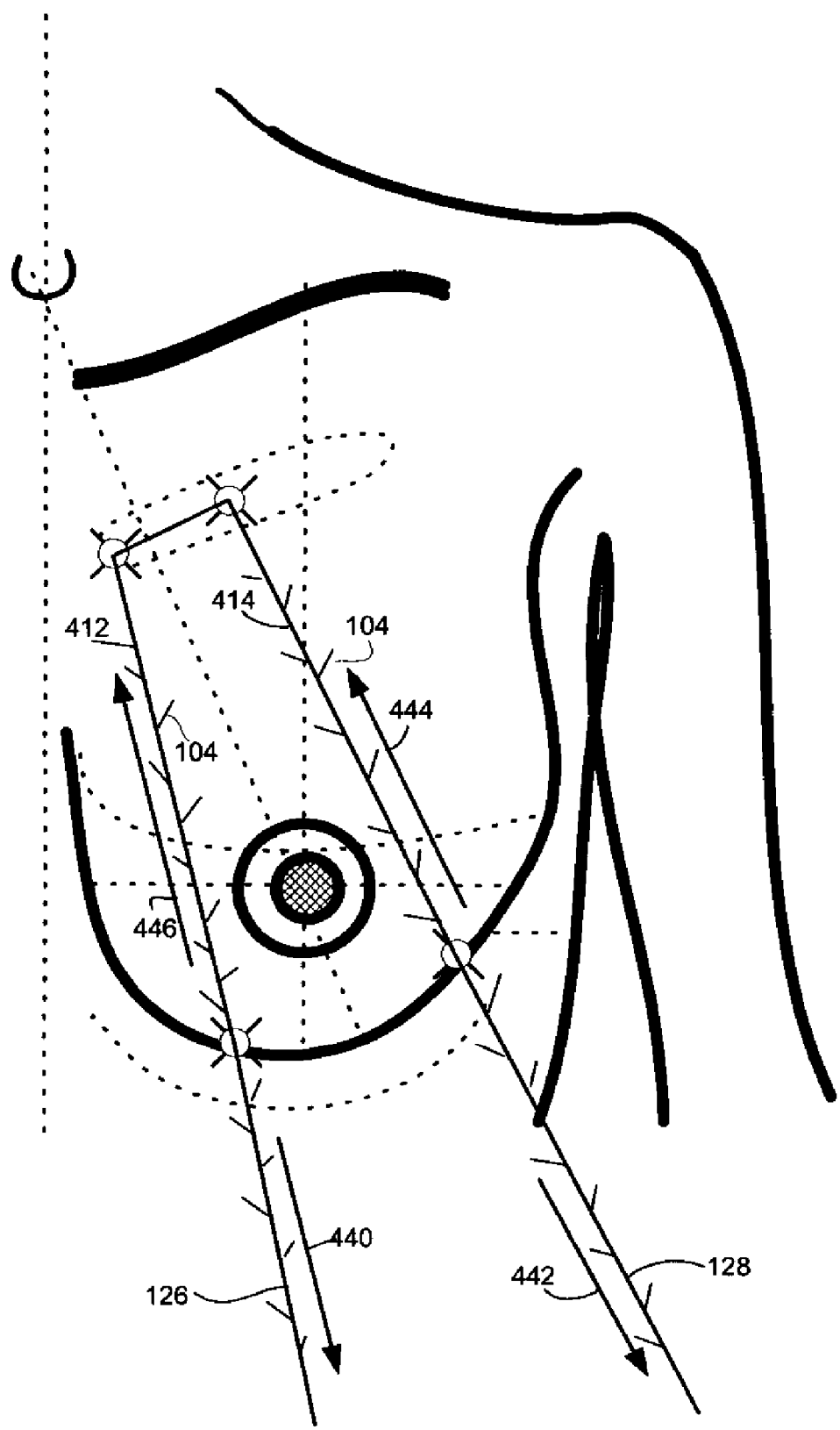

FIG. 4D illustrates the elevation step. In the elevation step, the physician applies light tension as shown by arrows 440, 442 to sections 126 and 128 of suture 100 outside of the patient's body. Section 126, 128 of suture 100 may be gripped by hemostats in order to facilitate application of tension. The application of tension to the suture maintains the suture stationary relative to the fixation points during elevation. The physician may then manually advance the patient's tissues along the barbed portions 126, 128 of suture 100 beneath deployment lines 412 and 414 in the direction shown by arrows 444 and 446 to achieve the desired lifting effect. Barbs 104 of both sections 126, 128 of suture 100 are oriented such that they yield toward the suture to allow the breast tissue to be elevated in the direction of arrow 446, 444. However, barbs 104 of suture 100 grasp the tissue and prevent it from moving in the direction opposite to arrows 444, 446. Thus, the suture maintains the elevation of the breast tissues relative to the anchor point. An advantage of the procedures of the present invention is that the barbs are oriented so as to support the tissue along the entire length of the deployed suture. This orientation of the barbs 104 provides support and contouring of the tissues along the entire length of the deployed suture.

During the elevation step, the physician may raise the patient to a sitting position to evaluate whether the desired amount of lifting has been achieved. The physician continues advancing the tissues along the sutures until in his judgment the desired aesthetic effect is achieved. If multiple sutures are deployed, the physician may deploy all the sutures prior to elevation. Alternatively, the physician may complete the elevation step with respect to a first suture before deciding upon the need for or placement of a second suture.

After the desired aesthetic effect has been achieved, the physician cuts off the excess suture material and closes the insertion and exit points. In one embodiment, ends of the suture 100 in the tissue are made to lie below the surface of the skin by first depressing the skin immediately around the ends and severing suture body 102 closely against the skin. The skin will rise to cover the ends of the suture 100. The puncture wounds may be closed in any suitable conventional manner. However, it is desired that the puncture wounds be closed in a manner that leaves no scarring.

FIGS. 5A-5L illustrate alternative deployment patterns that may be used in accordance with embodiments of the present invention. In each of FIGS. 5A-5L the suture is deployed in a similar manner to that described above with respect to FIGS. 4A-4D. In general, as previously described, a suture is first fixated at an insertion point (which could be a single puncture wound or a deployment line) to a stable anatomical feature such as the fascia pectoralis. The two ends of the suture are then deployed in a caudal or caudal and lateral direction through the selected breast tissues. The breast tissues are then elevated relative to the fixation point by applying light tension to the suture and manually grouping and advancing the tissue along the suture. In each of these deployments, barbs 104 are oriented such that barbs 104 retain and support the elevated tissues against gravity.

Figure 5A:
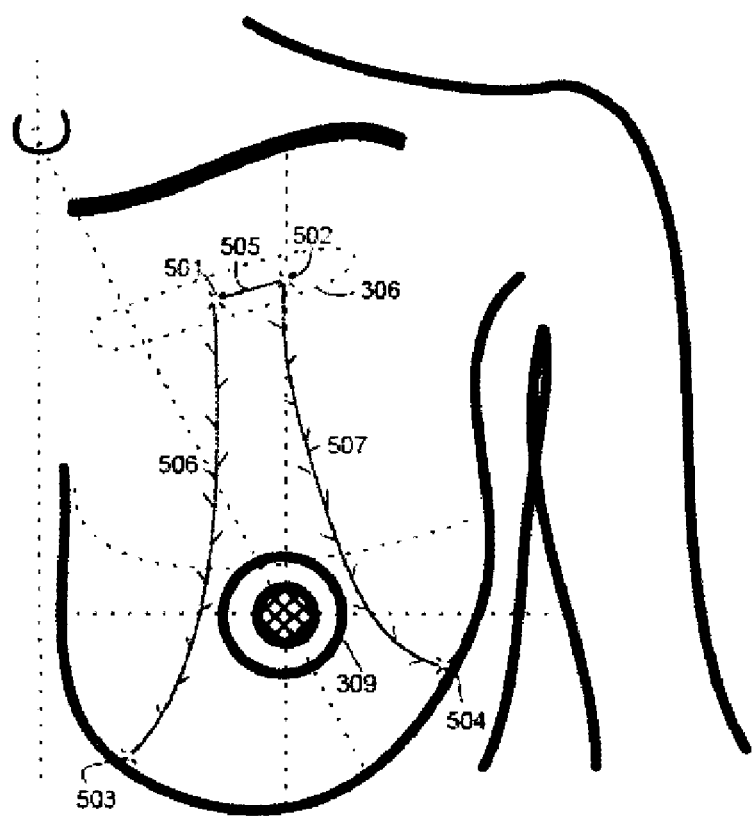
FIG. 5A-L show alternative deployments for breast-lift and/or NAC-lift procedures in accordance with different embodiments of the present invention.

FIG. 5A illustrates one alternative embodiment of the present invention. FIG. 5A shows insertion point 501, insertion-exit point 502, exit points 503, 504, and deployment lines 505, 506, 507. In this embodiment, the physician fixates a barbed suture by first deploying the suture from insertion point 501 to insertion-exit point 502. The physician may direct the suture though the fascia pectoralis over the second rib providing a stable anchor point for the suture. Optionally, the suture may also be directed through the periosteum of the second rib. The physician then deploys the suture from insertion point 501 along deployment line 506 to exit point 503 and from insertion-exit point 502 along deployment line 507 to exit point 504. Deployment lines 506 and 507 pass in a generally caudal direction to either side of NAC 309. After passing NAC 309, the more lateral deployment line 507 curves outward more laterally to exit point 504, while the more medial deployment line 506 curves more medially to exit point 503. In one embodiment, the suture is deployed at a shallow subcutaneous depth along deployment lines 506, 507 to contour the surface structures of the breast. This deployment pattern may be used to elevate the NAC with respect to the breast and also conize the breast by displacing tissues below the NAC towards the NAC.

Figure 5B:
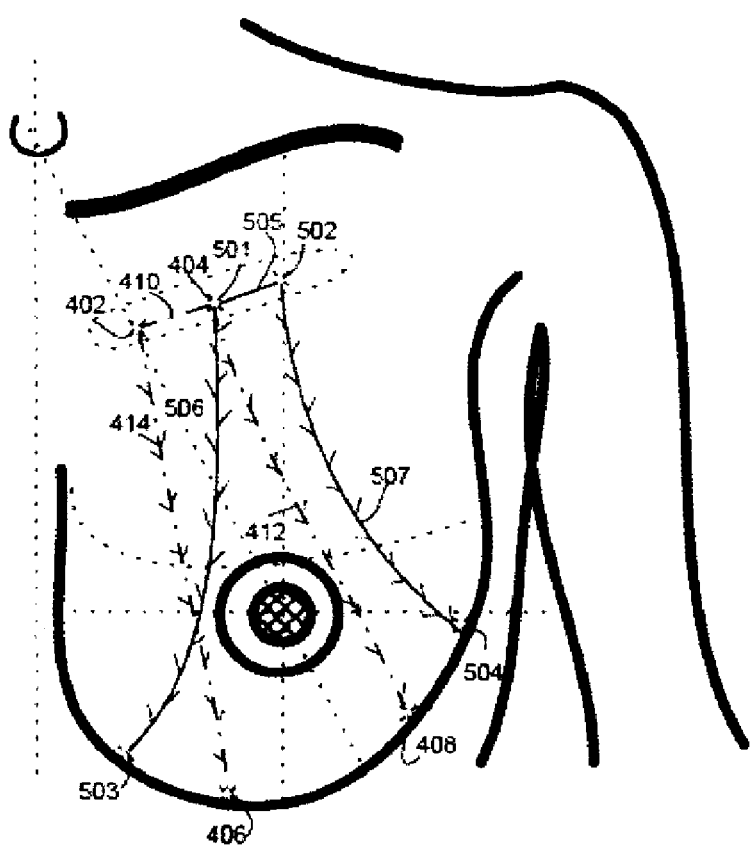

FIG. 5B illustrates one alternative embodiment of the present invention comprising a deployment pattern that utilizes two sutures. This deployment pattern combines the deployment pattern of FIG. 4A with the deployment pattern of FIG. 5A. In the combined deployment pattern, insertion-exit point 404 of the first suture is shared with insertion point 501 of the second suture. Both of these deployment points will be in the same puncture wound thereby reducing the number of puncture wounds required and reducing the potential for scarring. Depending on the particular anatomy of the patient it may be desirable that a larger or greater number of the puncture wounds be shared between sutures. The fewest number of puncture wounds should be utilized to achieve the desired deployment. In the one implementation of the deployment pattern of FIG. 5B, a first suture is deployed through deep fibrous and fatty parenchymal tissue of the breast along deployment lines 414 and 412 and a second suture is deployed through shallow subcutaneous tissues of the breast along deployment lines 506, 507. The first suture allows elevation of the breast, while the second suture allows elevation of the NAC relative to the breast and contouring of the surface of the breast. During the elevation step, tension will first be applied to the suture that has been deployed through the deep fibrous and fatty parenchymal tissue of the breast and this breast will be manually grouped and advanced along this suture until the desired breast-lift achieved. After the desired breast-lift is achieved, tension will then be applied to the suture deployed through the shallow subcutaneous tissues and the skin of the breast and the NAC will be manually grouped and advanced along this suture until the desired NAC-lift and contouring of the breast surface is achieved.

Figure 5C:
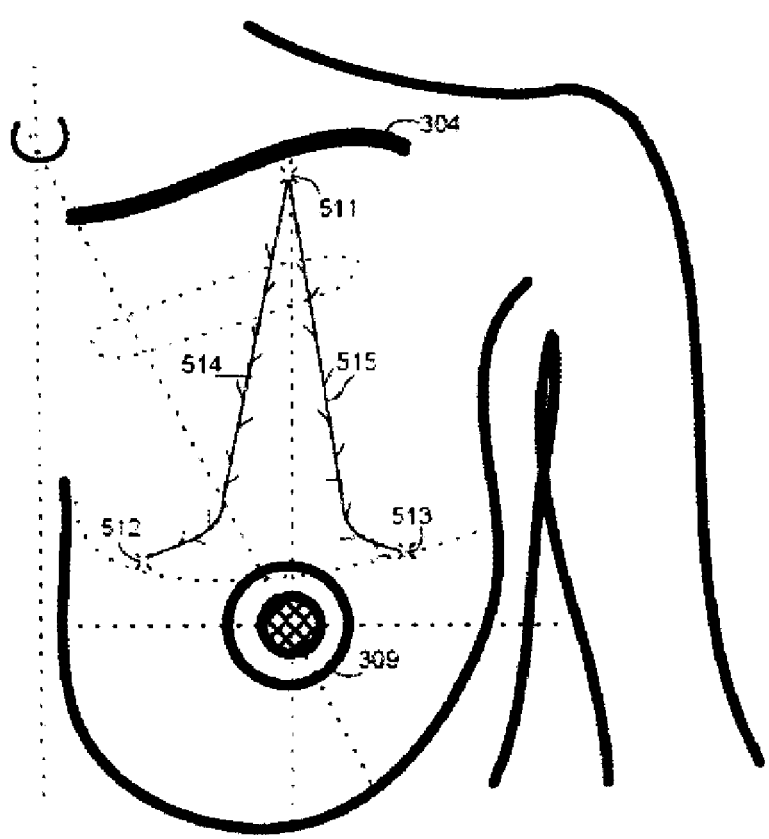

FIG. 5C illustrates one alternative embodiment of the present invention comprising a deployment in which insertion point 511 serves as both the insertion point and the first exit point. This reduces the number of puncture wounds required and thereby reduces the potential for scarring. The deployment pattern of FIG. 5C, comprises insertion-exit point 511, exit points 512, 513 and deployment lines 514, 515. Insertion point 511 is located proximate to clavicle 304. A suture is first fixated to the fascia pectoralis proximate to the clavicle at insertion point 511. Optionally, the suture may also be directed through the periosteum of the clavicle. The suture is then deployed in a generally caudal direction along deployment lines 514, 515 to exit points 512, 513 which are located one either side of NAC 309 and cranially of NAC 309. The deployment paths flare out to either side of the breast as they approach the NAC which allows tissues to be drawn in towards the vertical line 315 during the elevation step. The suture may be deployed through shallow subcutaneous tissues of the breast and this deployment to provide contouring of the surface of the breast including conization, and elevation of NAC 309 with respect to the breast.

Figure 5D:
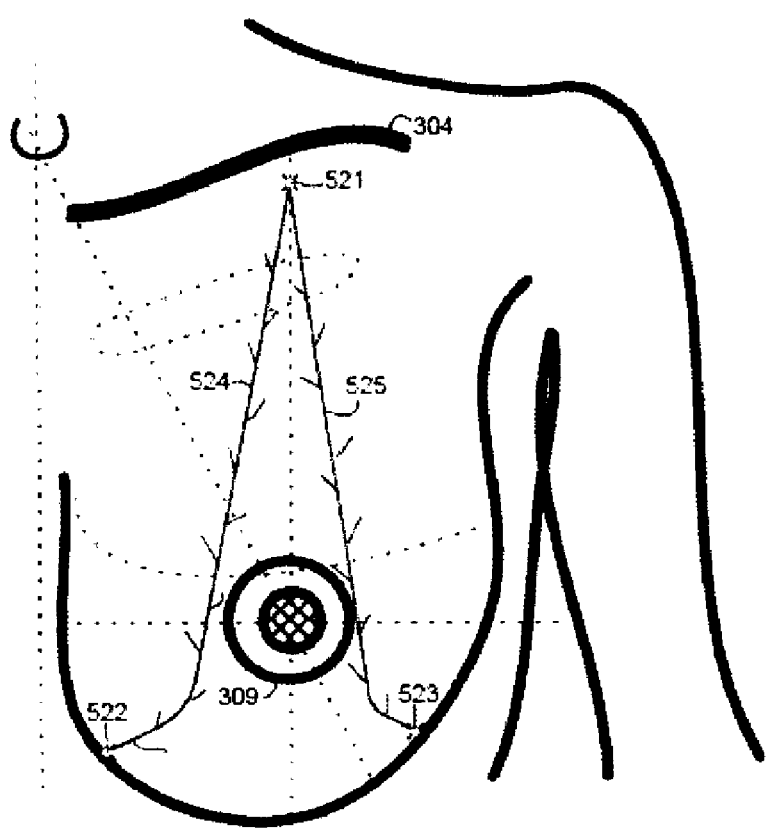

FIG. 5D also illustrates one alternative embodiment of the present invention comprising a deployment in which insertion point 521 serves both as the insertion point and as the first exit point. This reduces the number of puncture wounds required and reduces the potential for scarring. The deployment pattern of FIG. 5D comprises insertion-exit point 521, exits points 522, 523 and deployment lines 524, 525. Insertion-exit point 521 is located proximate to clavicle 304. A suture is first fixated to the fascia pectoralis proximate the clavicle at insertion-exit point 521. The suture is then deployed in a generally caudally direction along deployment lines 524, 525 to exit points 522, 523 which are located one either side of NAC 309 and caudally of NAC 309 on the lower curvature of the breast. The suture may be deployed through deep fibrous and fatty parenchymal tissue of the breast to allow for elevation of the breast as a whole.

Figure 5E:
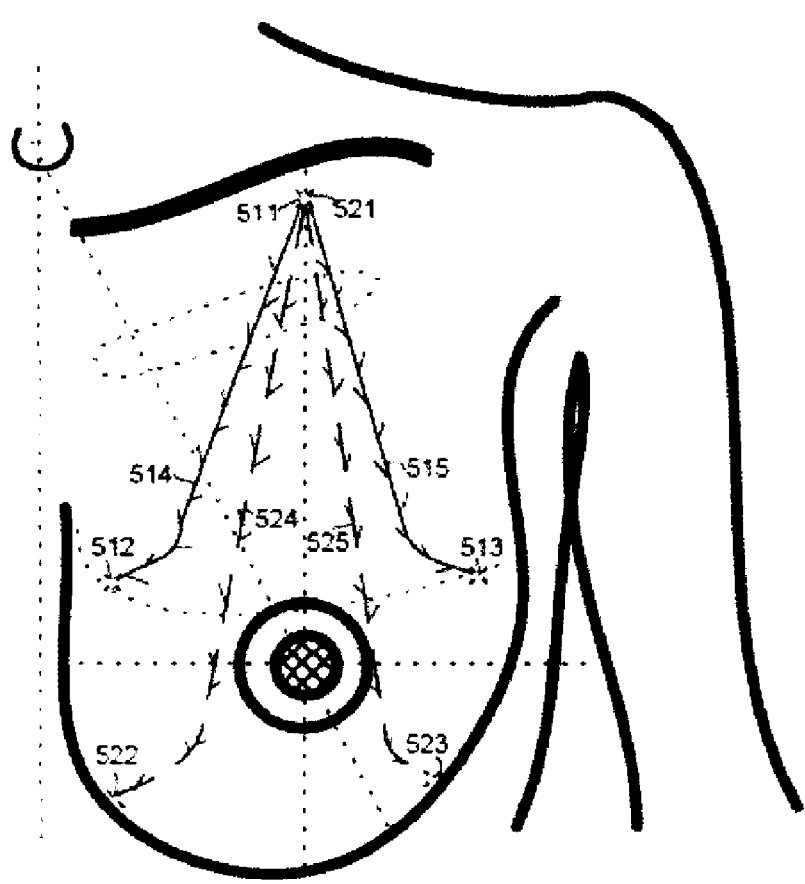
Figure 5F:
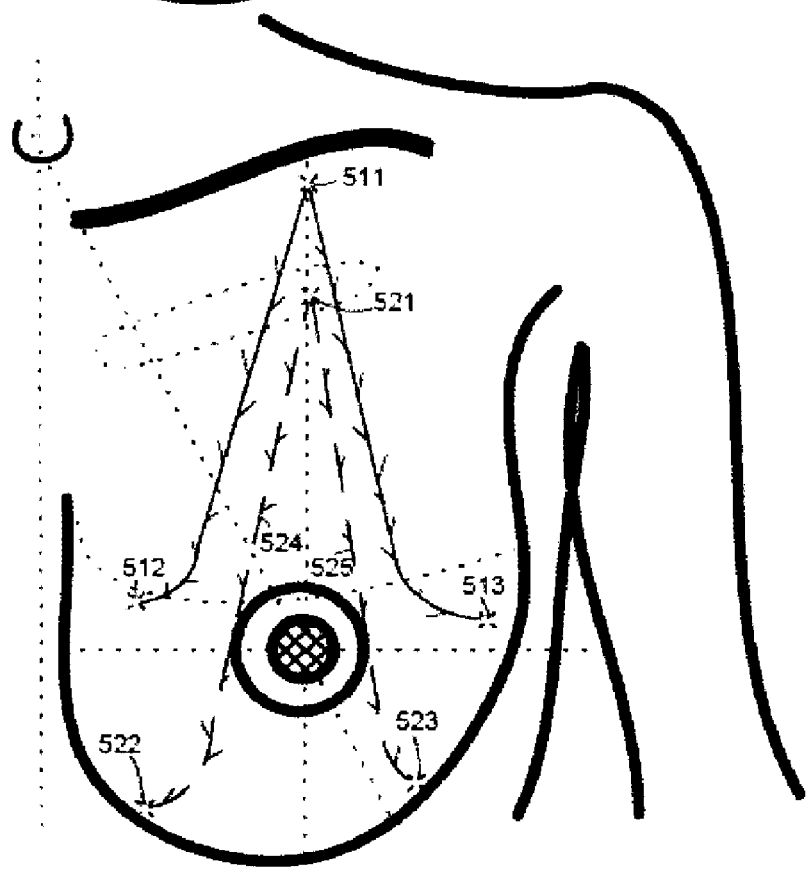

FIG. 5E illustrates one alternative embodiment of the present invention comprising a deployment pattern combining the deployment patterns of FIGS. 5C, 5D. As shown in FIG. 5E, insertion points 511, 521 may be located at the same point thereby reducing the number of puncture wounds required. In the implementation of this deployment pattern, a first suture is deployed along deployment lines 514, 515 through shallow subcutaneous tissue and a second suture is deployed through fibrous and fatty parenchymal tissue of the breast along deployment lines 524, 525. This deployment pattern allows for elevation of the breast as well as elevation of the NAC relative to the breast. FIG. 5F shows another deployment pattern combining the deployment patterns of FIGS. 5C, 5D except that that insertion points 521 and 511 are not located at the same point. Instead, insertion point 521 is displaced caudally of insertion point 511. As with the two-suture deployment of FIG. 5B, the elevation of the breast utilizing the deployment pattern of FIGS. 5E, 5F may also be performed in two stages. First, elevation of the breast along the deep suture, and second, when the breast has been elevated, elevation of the NAC and contouring of the skin along the shallow suture.

Figure 5G:
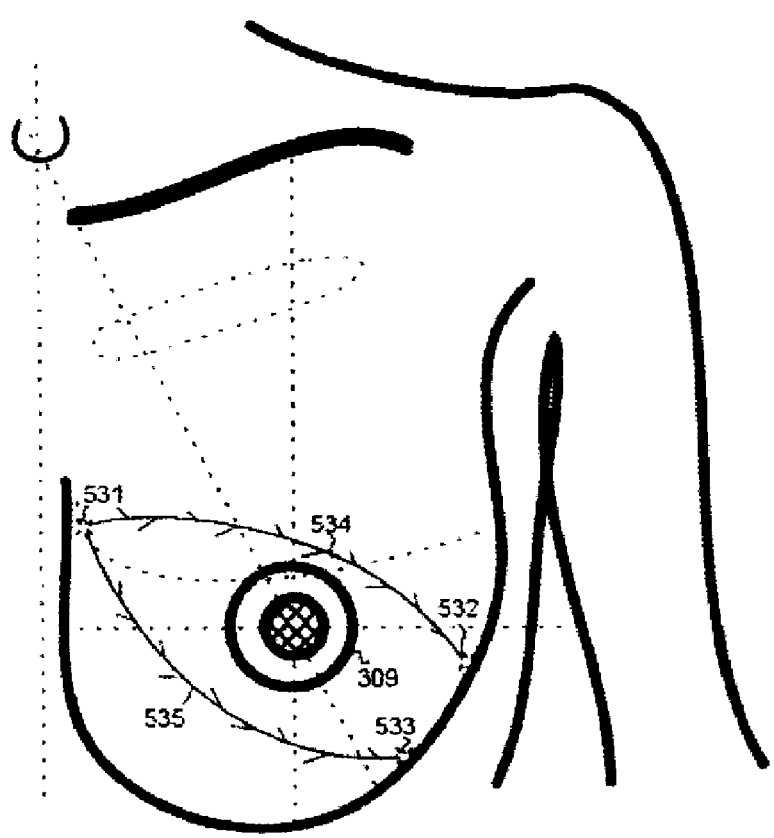

FIG. 5G illustrates another embodiment of the present invention. As shown in FIG. 5G, the deployment pattern comprises insertion-exit point 531, exit points 532, 533 and deployment lines 534, 535. Insertion-exit point 531 is located on the upper curvature of the breast proximate to the midline. At the insertion-exit point the barbed suture may be fixated to the fascia pectoralis proximate to the sternum. After fixation, the suture is deployed caudally and laterally along deployment lines 534 and 535 towards exit points 532, 534 on the lower curvature of the breast. The deployment lines may pass through deep fatty and fibrous tissue of the breast parenchyma. The deployment lines allow for elevation of the breast and repositioning of the breast towards the midline.

Figure 5H:
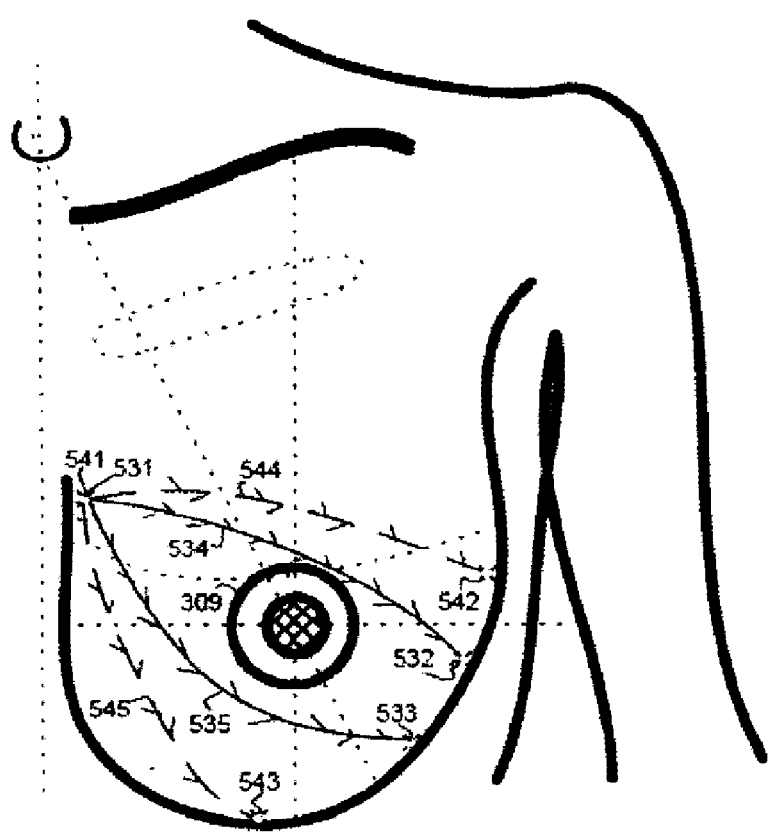
Figure 5I:
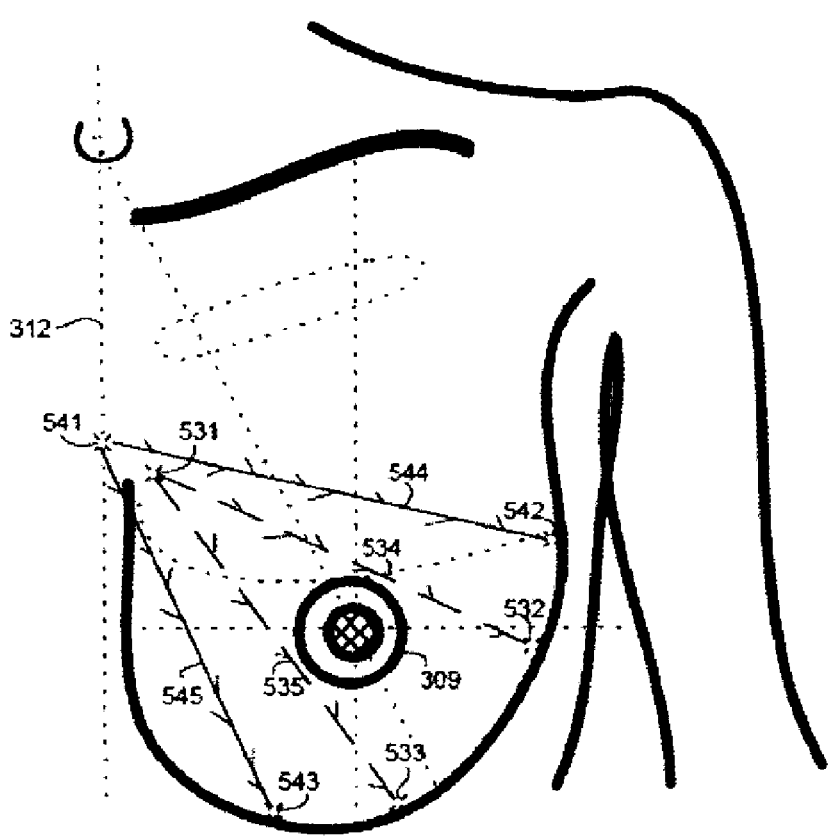

FIG. 5H illustrates the deployment pattern of FIG. 5G in combination with a second suture. The deployment of the second suture comprises insertion-exit point 541, exit points 542, 543 and deployment lines 544, 545. Insertion-exit point 541 is shown at the same location as insertion-exit point 531, however it may also be displaced slightly from insertion point 541. In one implementation a second suture is fixated to the fascia pectoralis proximate the sternum at insertion point 541. The suture is then deployed caudally and laterally along deployment lines 544, 545 to exit points 542, 543. Deployment may be through subcutaneous tissues to allow for surface contouring and elevation of the NAC relative to the breast. FIG. 5I illustrates an alternative embodiment of the deployment pattern of FIG. 5H. As shown in FIG. 5I, insertion point 541 is displaced more medially than insertion point 531 and is positioned over the sternum. The sternum provides a stable anchor point as the fascia pectoralis is attached to the front of the sternum.

Figure 5J:
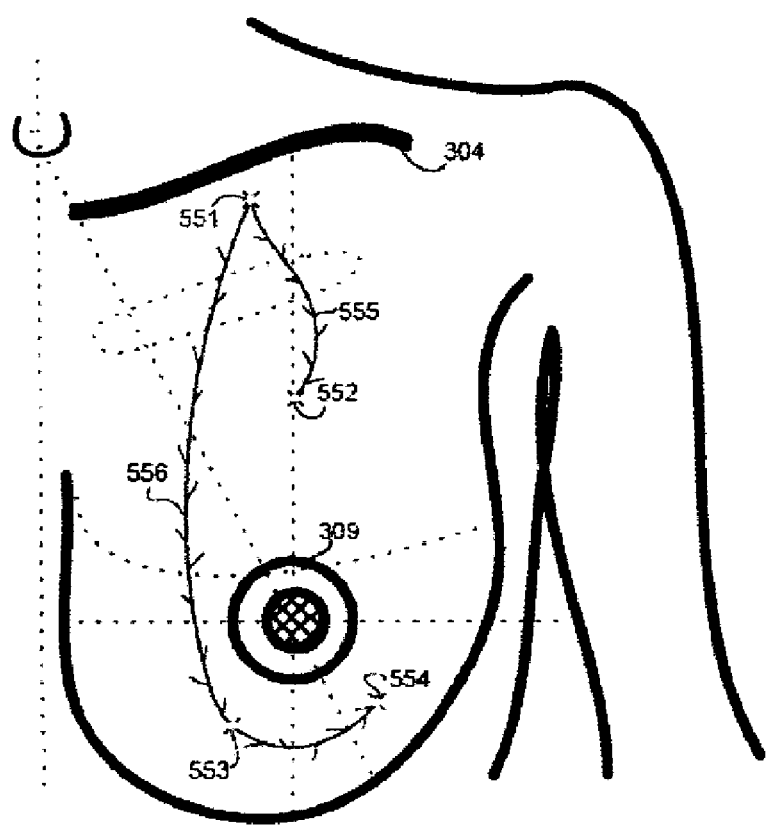

FIG. 5J illustrates an alternative deployment pattern. As shown in FIG. 5J, deployment pattern comprise insertion point 551 proximate clavicle 304, insertion-exit point 553 and exit points 552, 554. The pattern is implemented by fixating the suture to the fascia pectoralis at insertion point 551 and then deploying the suture along deployment lines 555, 556 towards exit points 553, 554. Exit point 552 is shown located at approximately the level of the third rib. Deployment line 556 passes first through insertion-exit point 553. At insertion-exit point 553 the suture is brought out through the skin and then reintroduced through the same point. This insertion-exit point allows for the direction of the deployment line to be changed. Although the deployment lines may be curved, there is a limit to how sharp a change in needle direction may be made. If a sharp change in deployment direction is desired, an intermediate insertion-exit point may be useful in order to accomplish the change in direction.

Figure 5K:
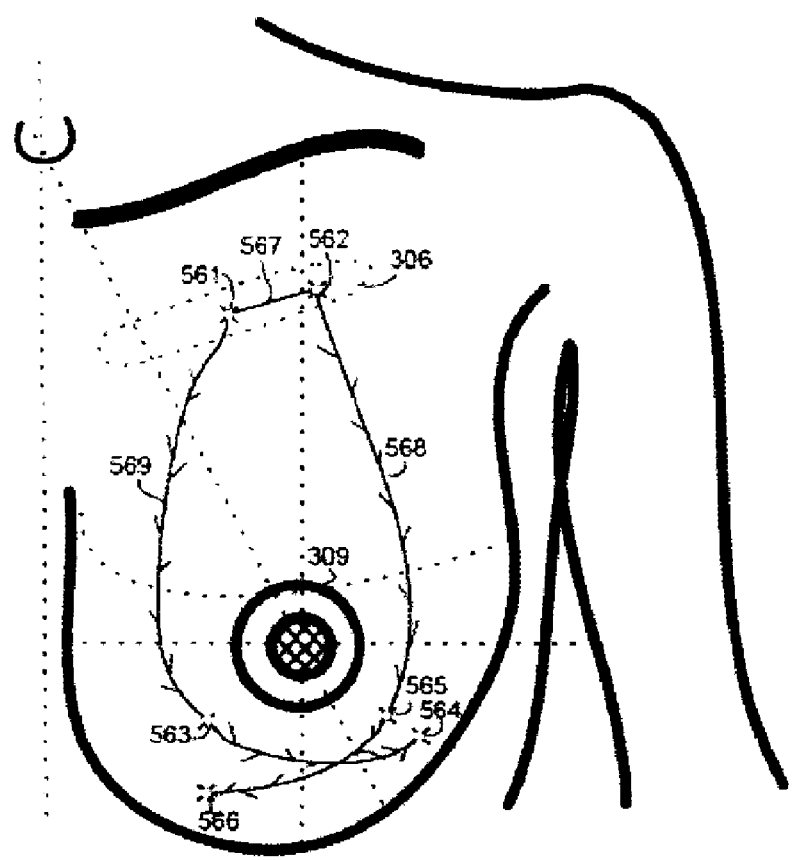

FIG. 5K illustrates a variation on the deployment pattern of FIG. 5J. In this deployment, a suture is first anchored through the fascia pectoralis over second rib 306 along deployment line 567. Both ends of the suture are then deployed caudally to either side of NAC along deployment lines 568, 569 to exit points 566, 564 on the lower curvature of the breast. Intermediate insertion-exit points 563 and 565 may be utilized if necessary to achieve the desired curvature in the deployment trajectory. A suture deployed in this fashion can cradle the breast tissue allowing for elevation of the breast and NAC during the elevation step.

Figure 5L:
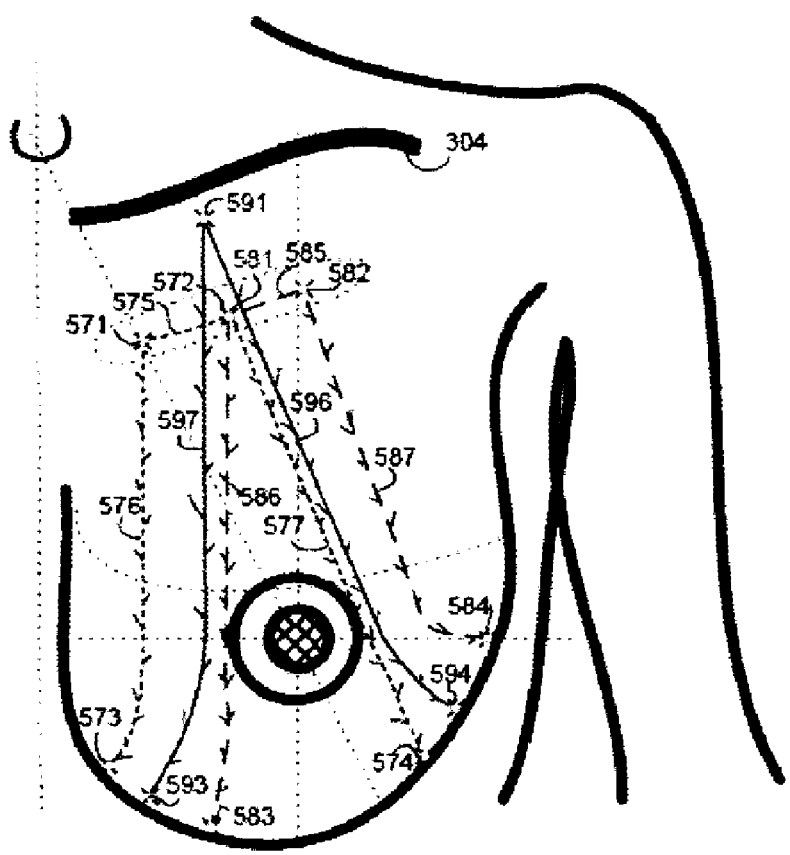

FIG. 5L illustrates a deployment pattern involving three bidirectional sutures. Referring to FIG. 5L, the deployment lines for each of the three sutures are shown with a distinct line pattern. The deployment pattern for the first suture, indicated by the small-dash line, comprises insertion point 571, insertion-exit point 572, exit points 573, 574 and deployment lines 575, 576, 577. The first suture is deployed by first fixating the suture to the fascia pectoralis proximate the second rib along deployment line 575 between insertion point 571 and insertion-exit point 572; deploying one end of the suture caudally from insertion point 571 to exit point 573; and deploying the other end caudally from insertion-exit point 572 to exit point 574. The deployment pattern for the second suture, indicated by the large-dash line, comprises insertion point 581, insertion-exit point 582, exit points 583, 584 and deployment lines 585, 586, 587. The second suture is deployed by first fixating the suture to the fascia pectoralis proximate the second rib along deployment line 585 between insertion point 581 and insertion-exit point 582; deploying one end of the suture caudally from insertion point 581 to exit point 583; and deploying the other end caudally from insertion-exit point 582 to exit point 584. The deployment pattern for the third suture, indicated by the solid line, comprises insertion point 591, exit points 593, 594 and deployment lines 596, 597. The third suture is deployed by first fixating the suture to the fascia pectoralis proximate the clavicle at insertion point 591; deploying one end of the suture caudally from insertion point 591 to exit point 593; and deploying the other end caudally from insertion point 591 to exit point 594. The first and second sutures may be deployed through deeper fatty and fibrous parenchymal tissues of the breast to allow elevation of the breast. The third suture may be deployed through shallow subcutaneous tissue to position the NAC and contour the skin of the elevated breast. In practice, all three sutures may be deployed prior to elevation. During the first stage of the elevation step, the first and second (deep) sutures will be held under tension while the breast is advanced along deployment lines 576, 586, 577, 587. Finally, after the desired breast elevation is achieved, the third suture will be held under tension and the skin of the breast and the NAC will be advanced along deployment line 596, 597 until the NAC is at the desired height and the skin of the breast has the aesthetic contour desired.

Figure 6A:
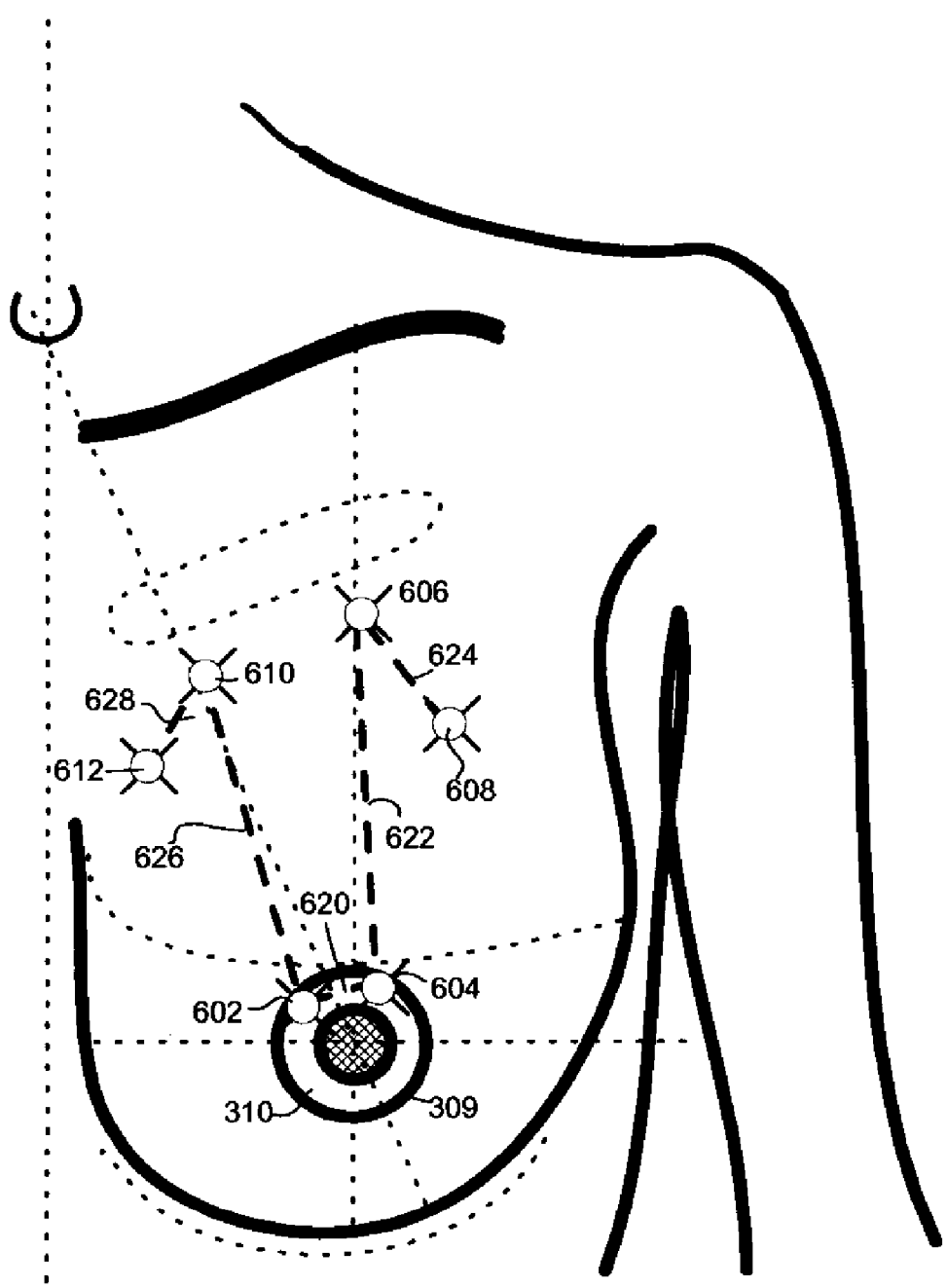
FIGS. 6A-D show the steps of a method for a NAC-lift procedure according to one embodiment of the invention.
Figure 6B:
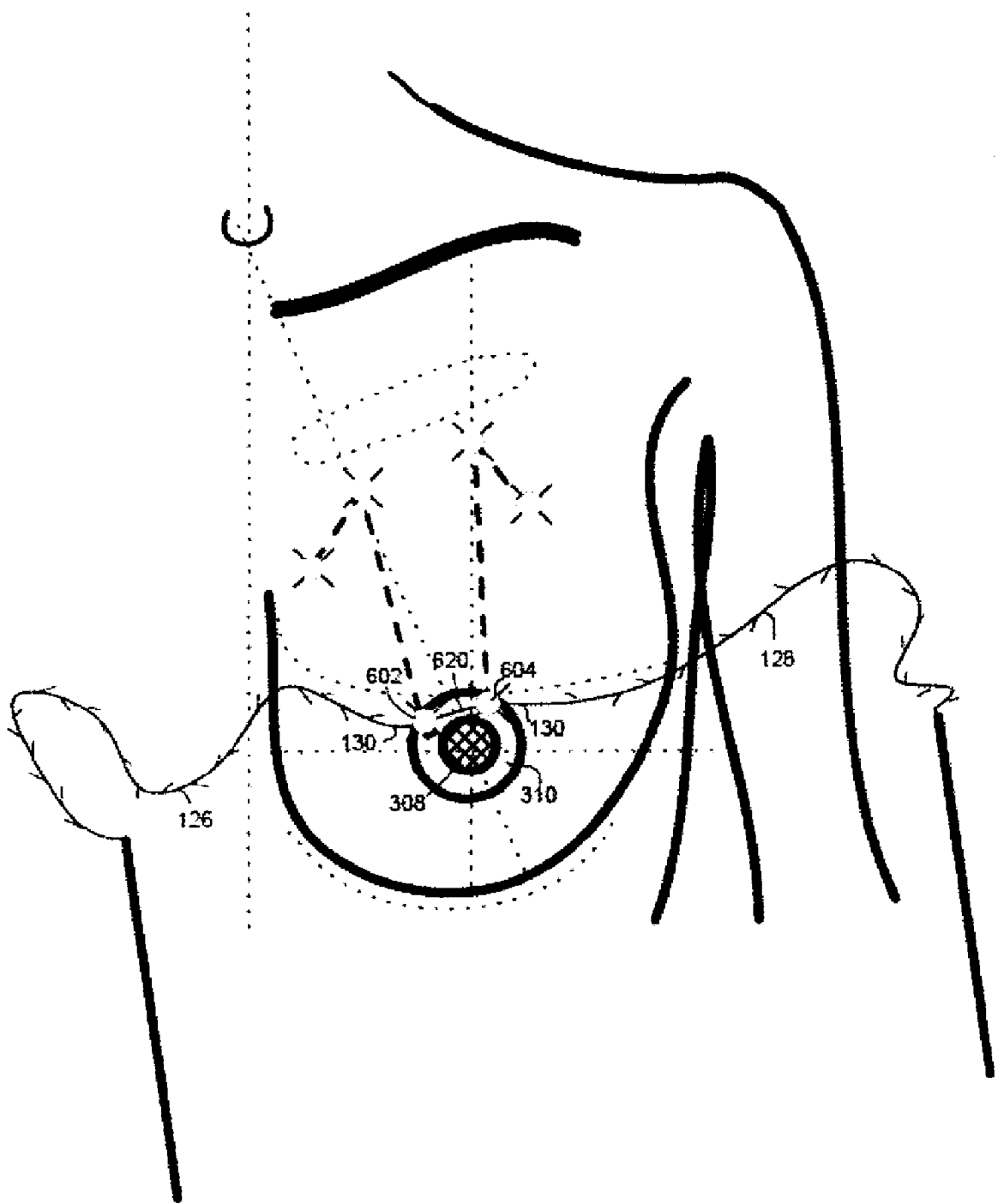

FIGS. 6A-6D illustrate an alternative method of suture deployment for lifting the NAC relative to the breast. As shown if FIG. 6A, the deployment pattern comprises insertion point 602, insertion-exit points 604, 606, 610, exit points 608, 612, and deployment lines 620, 622, 624, 626 and 628. As shown in FIG. 6B, suture 100 is introduced at insertion point 602 and deployed along deployment line 620 to insertion-exit point 604. Both insertion point 602 and insertion-exit point 604 are located in the areolus 310 surrounding nipple 308. Suture 100 is drawn along deployment line 620 until the unbarbed section 130 of suture 100 is located along deployment line 620. A little portion of unbarbed section 130 of suture 100 may protrude from insertion point 602 and insertion-exit point 604 at this stage as shown in FIG. 6B.

Figure 6C:
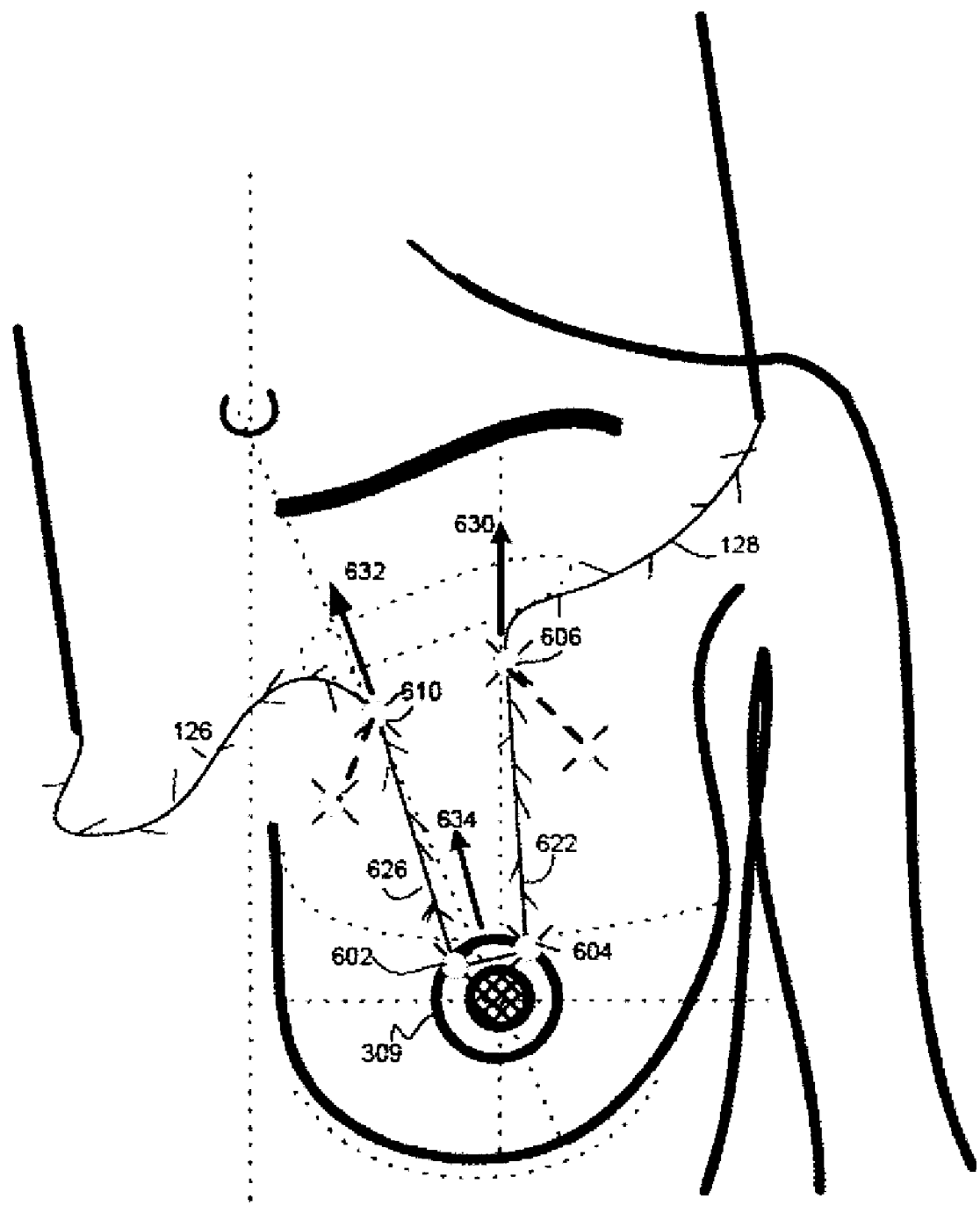

As shown in FIG. 6C, suture 100 is then deployed cranially from insertion point 602 along deployment line 626 to insertion-exit point 610. Likewise, suture 100 is deployed cranially from insertion-exit point 604 along deployment line 622 to insertion-exit point 606. The deployment is through shallow subcutaneous tissues. After deployment has reached this point, the NAC may be elevated into the desired position by drawing suture 100 upward as shown by arrows 630, 632, through insertion-exit points 606, 610. In one embodiment NAC 309 is elevated, in the direction shown by arrow 634, from 1 cm to no more than 3 cm. This degree of elevation permits the NAC to be elevated without elevating the breast tissue. In an alternative embodiment, the NAC can be raised more than 3 cm and the breast may also be elevated to some extent. The barbs on the suture are oriented to restrict the suture from being drawn back through the exit points after the NAC has been elevated.

Figure 6D:
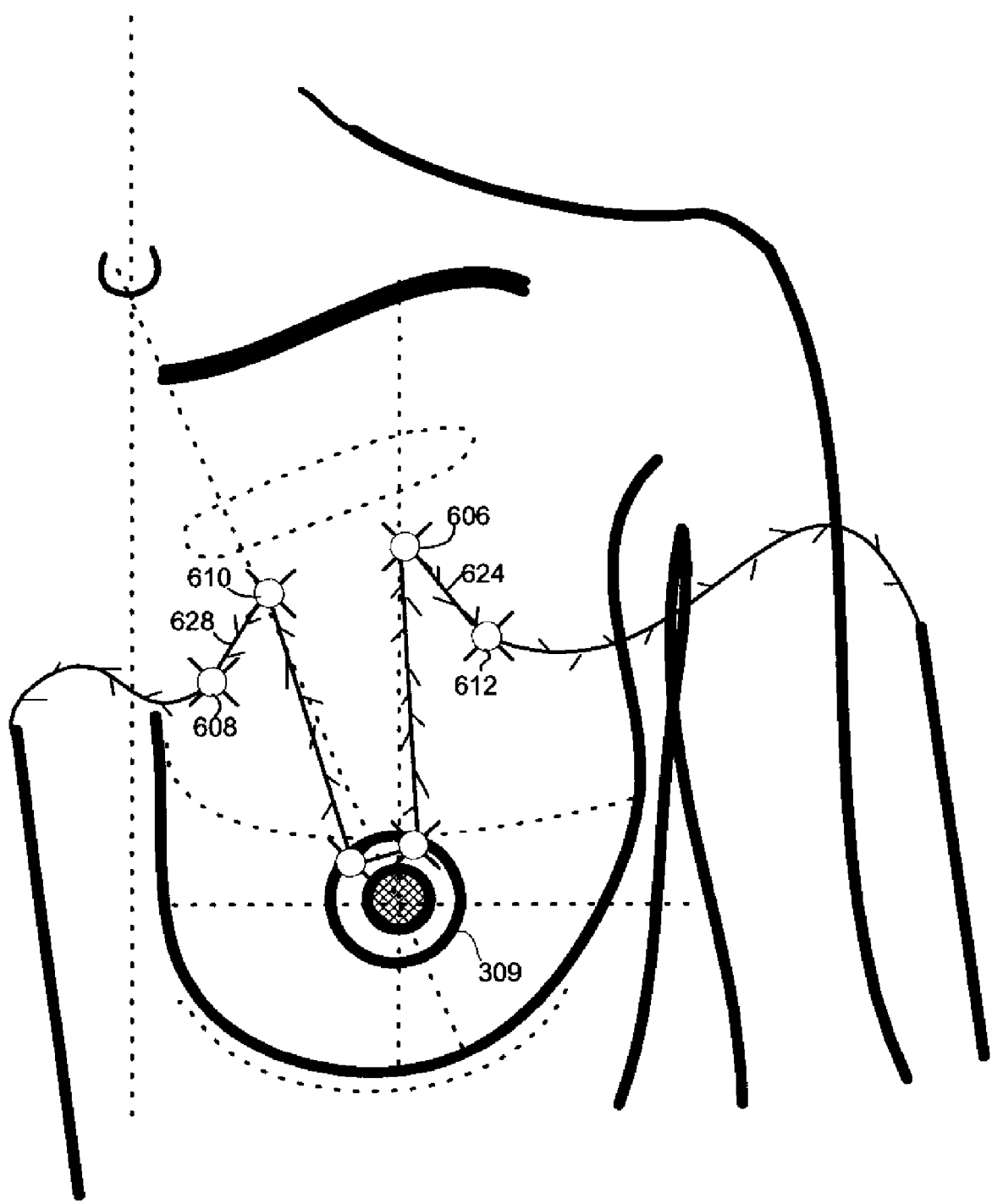

As shown in FIG. 6D, after the NAC has been elevated by the desired amount, the suture is deployed from insertion-exit point 606 along deployment line 624 through the fascia pectoralis to exit point 608. Likewise, the suture is deployed from insertion-exit 610 along deployment line 628 through the fascia pectoralis to exit point 612. The deployment through the fascia pectoralis fixates the ends of the suture thereby stabilizing the elevation of NAC 309. The needles and excess suture may then be removed and the puncture wounds closed as previously described. In an alternative deployment, instead of fixating suture 100 in the fascia pectoralis with a further caudal deployment, suture 100 may be fixated to the fascia pectoralis at exit points 606, 610 using a surgeon's knot. If necessary or desired, a second bidirectional suture may be deployed in a similar manner to the first with the second deployment pattern displaced from the first.

The NAC-lift procedure of FIGS. 6A-D may be used in combination with the deployment of other sutures to elevate the breast as shown in any of FIGS. 4A-D and 5A-K. A combination of breast-lift and nipple-lift using barbed sutures allows the surgeon to achieve many of the effects of a conventional mastopexy procedure without large incisions. One embodiment of a surgical procedure which combines both a breast-lift and a NAC-lift is shown in FIGS. 7A-D. The deployment pattern of FIGS. 7A-D employs three bidirectional sutures. The combination of three sutures in this way allows for control of breast-lift as well as NAC-lift relative to the breast and contouring of the breast to enhance conization.

Figure 7A:
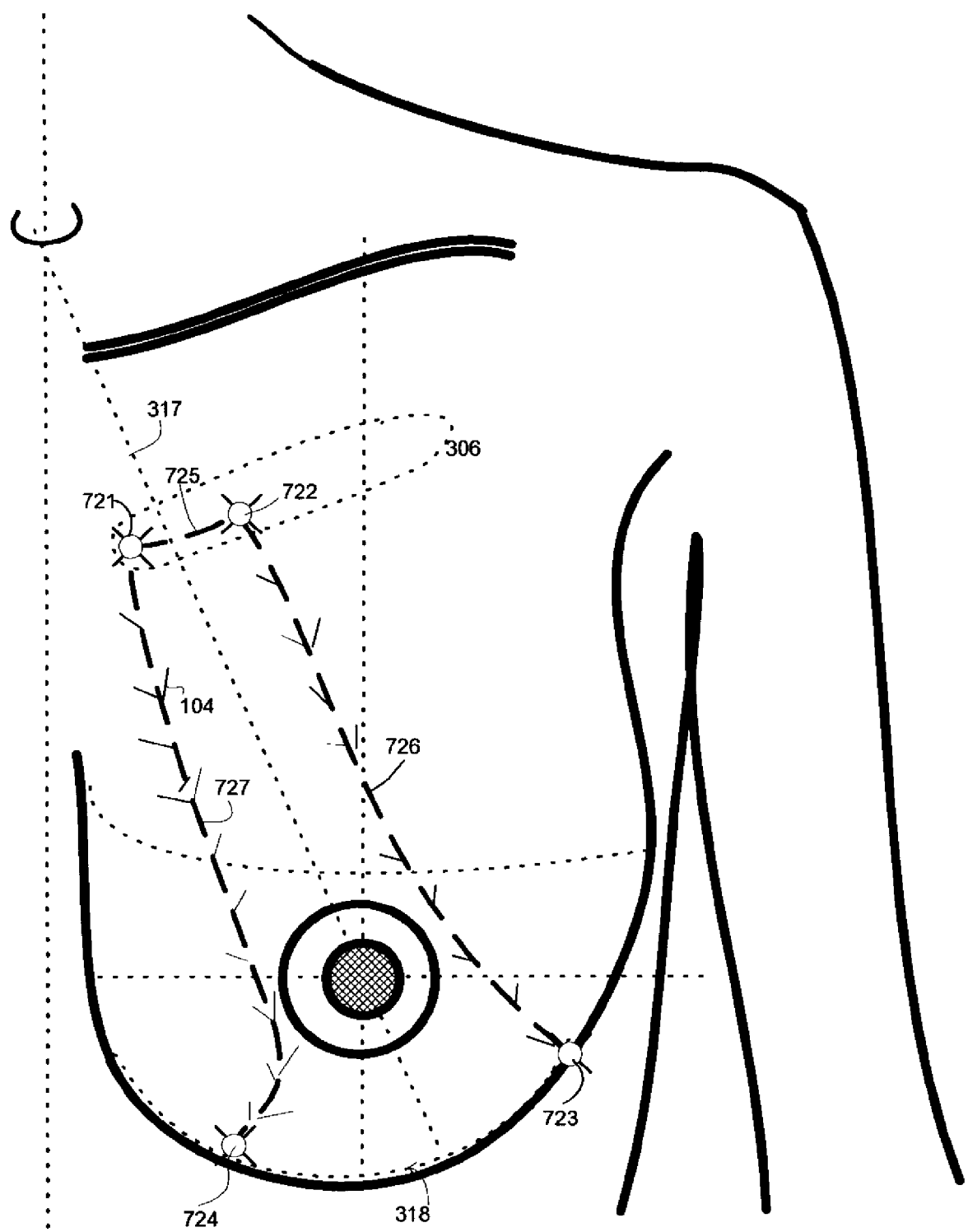
FIGS. 7A-D show the steps for a combination breast-lift and NAC-lift procedure according to one embodiment of the present invention.

A first suture 100 is deployed as shown in FIG. 7A. The deployment pattern comprises insertion point 721, insertion-exit point 722 and exit points 723 and 724. Insertion point 721 is over the second rib 1 cm medial of natural breast vector line 317. Insertion point 722 is over the second rib 1 cm lateral of natural breast vector line 317. Exit points 724 are both on lowest contour line 318. A fourteen gauge angiocatheter is looped between insertion points 721 and 722 gathering up the fascia pectoralis and the posterior lamella of the breast fascia overlying the second rib. A first needle is then inserted in retrograde fashion into the tip of the angiocatheter and pushed through the angiocatheter until the tip of the needle exits the insertion point of the angiocatheter. The angiocatheter is then removed and the tip of the needle can be grasped and drawn out of the insertion point. Suture 100 can then be drawn through the deployment path 725 until unbarbed section 130 lies between the two insertion points 721, 722, with a little of unbarbed section 130 remaining at each insertion point. One end of a suture is then deployed caudally along deployment line 727 from insertion point 721 to exit point 724. The other end of the suture is then deployed caudally along deployment line 726 from insertion point 722 to exit point 723. The deployment depth is selected so that the suture passes through deep fatty and fibrous parenchymal tissue in the middle of the breast gland. Note that the deployment angles out immediately below transthelial line 314. The suture can then be drawn along deployment lines 726, 727 until no portion remains above the skin at insertion points leaving the barbed sections of the suture within the breast tissue with the barbs 104 oriented as shown.

Figure 7B:
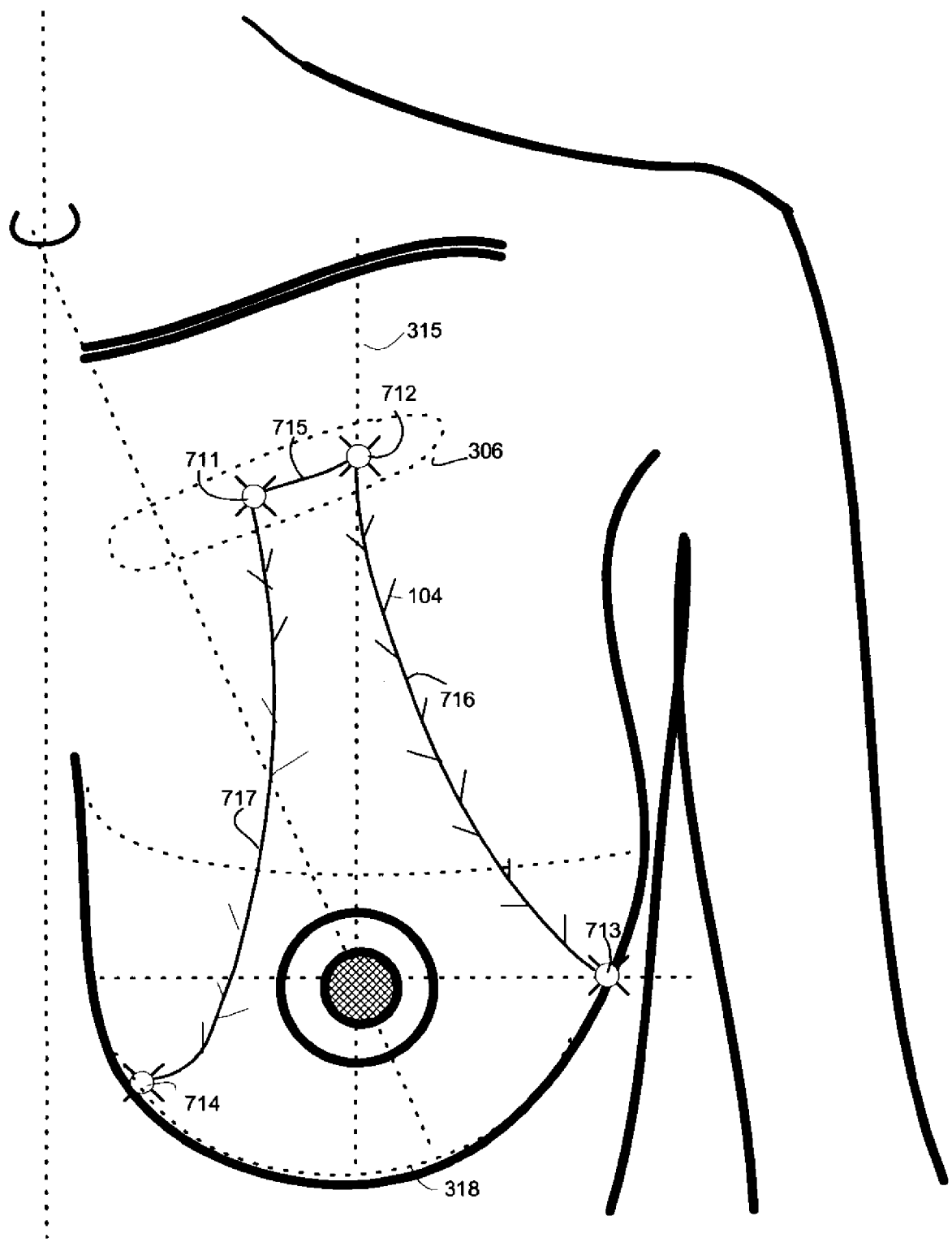
Figure 7C:
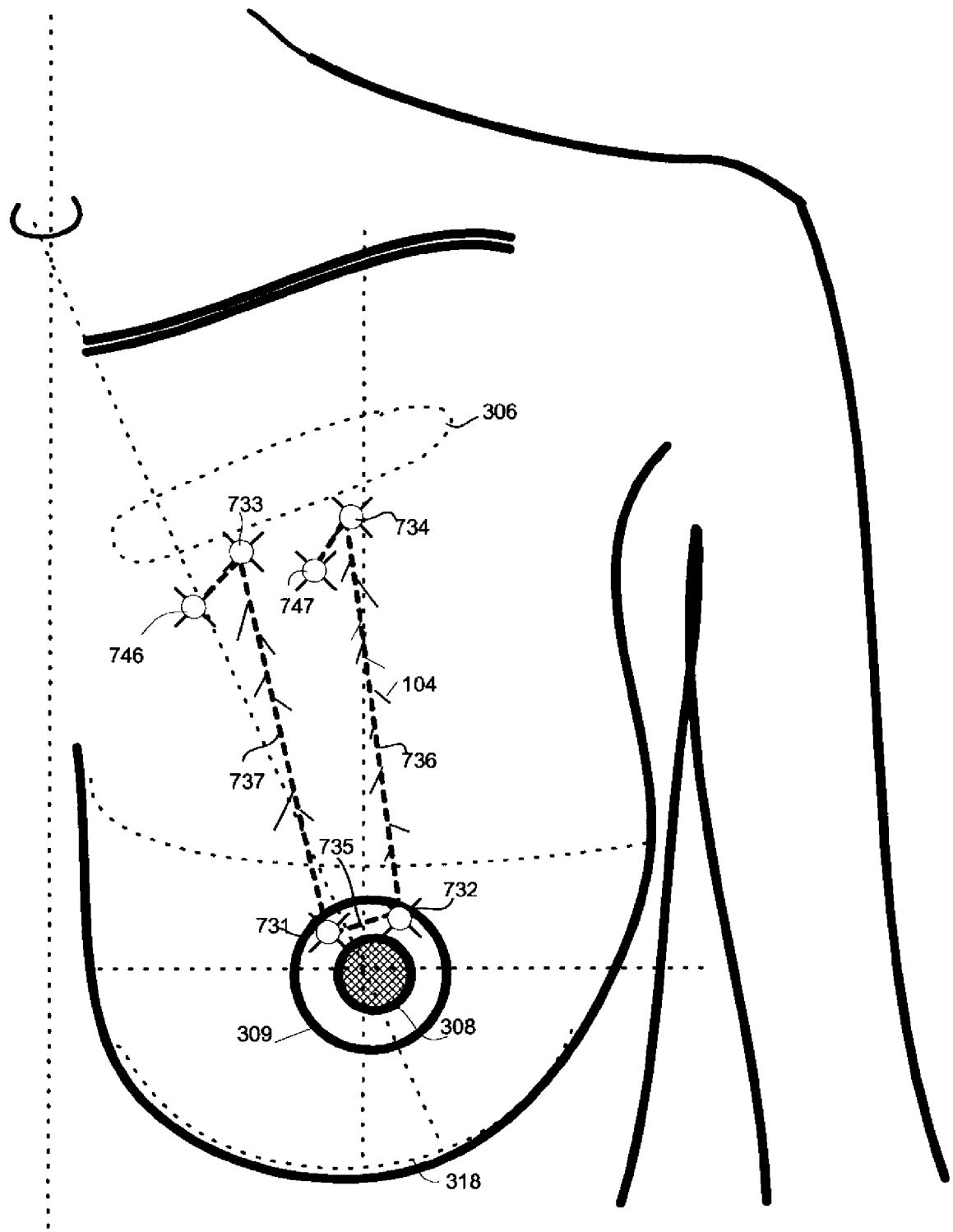
Figure 7D:
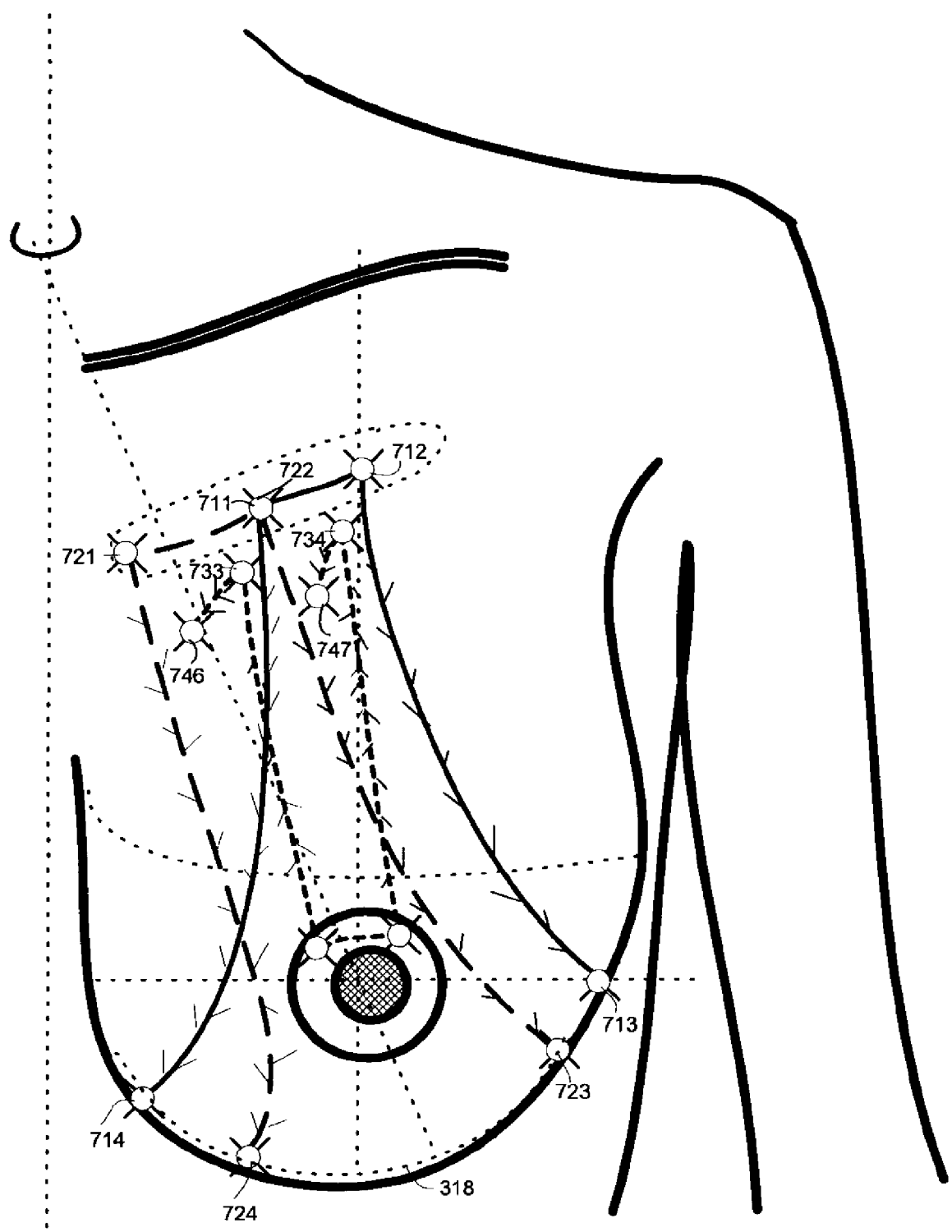

A second suture 100 is then deployed as shown in FIG. 7B. The deployment pattern comprises insertion point 711, insertion-exit point 712 and exit points 713 and 714. In this deployment, insertion points 711 and 722 share the same location, reducing the number of punctures necessary. Insertion point 712 is placed over the second rib between insertion point 722 and vertical line 315 at a position selected based on the elevation axis desired. A fourteen gauge angiocatheter is looped between insertion points 711 and 712 gathering up the fascia pectoralis and the posterior lamella of the breast fascia overlying the second rib. A first needle is then inserted in retrograde fashion into the tip of the angiocatheter and pushed through the angiocatheter until the tip of the needle exits the insertion point of the angiocatheter. The angiocatheter is then removed and the tip of the needle can be grasped and drawn out of the insertion point. Suture 100 can then be drawn through the deployment path 715 until unbarbed section 130 lies between the two insertion points 711, 712, with a little of unbarbed section 130 remaining at each insertion point. One end of a suture is then deployed caudally along deployment line 717 from insertion point 711 to exit point 714. The other end of the suture is then deployed caudally along deployment line 716 from insertion point 712 to exit point 713. The deployment depth is selected so that the suture passes through deep fatty and fibrous parenchymal tissue in the middle of the breast gland. Note that the deployment angles out immediately below transthelial line 314. The suture can then be drawn along deployment lines 716, 717 until no portion remains above the skin at insertion points leaving the barbed sections of the suture within the breast tissue with the barbs 104 oriented as shown. The second suture, may alternatively be deployed at a more shallow depth if sufficient elevation is expected with the first suture, or more contouring of the breast surface is desired.

After the deployment of the first two sutures as shown in FIGS. 7A, 7B, the breast may be elevated by grouping and advancing the breast tissue along the long deployment lines 716, 717, 726, 727 of the first and second bidirectional (deep) sutures while maintaining tension on the free ends of the first and second bidirectional (deep) sutures. The elevation step is performed with the patient in an upright position in order to gauge the aesthetic effects achieved. Because these sutures are deployed in the deeper fatty and fibrous parenchymal tissues of the breast, the grouping and advancing of the breast tissue elevates the breast as a whole towards second rib 306.

A third bidirectional suture is then deployed as shown in FIG. 7 C. The deployment pattern comprises insertion point 731, insertion-exit point 732, 733 and 734. Insertion point 731 and insertion-exit point 732 are located in NAC 309 above nipple 308. Insertion-exit points 733 and 734 may be located over the third rib on vectors from NAC 309 along which NAC 309 is desired to be positioned. The NAC will have moved during the elevation of the breast gland and so the location of these insertion-exit points may be selected after breast elevation to achieve the desired location of NAC 309 on the elevated breast. As shown in FIG. 7C, the third suture is deployed between insertion point 731 and insertion-exit point 732 along deployment line 735. A needle is first inserted at insertion point 731 and pushed through the tissues of the NAC and out insertion-exit point 732. The deployment depth is through shallow structures of the NAC but the deployment depth is deep enough to avoid extrusion of the suture over time. Suture 100 is then drawn along deployment line 735 until the unbarbed section 130 of suture 100 is located along deployment line 735 within the tissues of the NAC. The suture is then deployed cranially along deployment lines 736, 737 to exit points 733, 734 proximate the third rib. The deployment depth is controlled such that the third suture is deployed through shallow subcutaneous tissue.

The NAC may then be repositioned relative to the breast. This is achieved by applying tension to the third bidirectional suture and pulling the suture up through the insertion-exit points 733, 734 proximate the third rib. When the desired NAC position has been achieved the suture is deployed in a downward direction from insertion-exit points 733, 734 to exit points 736, 737. The suture penetrates through the fascia pectoralis between insertion-exit points 733, 734 and exit points 736, 737 thus anchoring the suture to a stable anatomical feature in order to maintaining the desired position of the NAC.

The position of the breast tissues on the three sutures may be adjusted by the physician with the patient in an elevated position until the physician, in his or her judgment, has achieved the aesthetic result desired. After the elevation is complete to the physician's satisfaction, the free ends of the suture may be cut off and the exit wounds closed. This embodiment of the present invention, by utilizing a combination of three sutures, allows for control of breast-lift, as well as positioning the NAC relative to the breast and contouring the tissues above the NAC.

The foregoing description of embodiments of the present invention has been provided for the purposes of illustration and description. It is not intended to be exhaustive or to limit the invention to the precise forms disclosed. The deployment patterns described may be modified and combined in accordance with the principles described to provide the breast and NAC elevation, medial displacement and contouring desired in a particular case in light of the patient's anatomy. Many embodiments were chosen and described in order to explain the principles of the invention and its practical application, thereby enabling others skilled in the art to understand the invention for various embodiments and with various modifications that are suited to the particular use contemplated. It is intended that the scope of the invention be defined by the claims and their equivalents.

The invention claimed is:

1. A method of performing a cosmetic procedure to reposition portions of a breast having a nipple-areola complex (NAC) using a first suture including a plurality of barbs, the barbs on a first portion of the first suture between a first end of the first suture and a first axial location on the first suture for permitting movement of the first suture through tissue in a direction of movement of the first end and preventing movement of the first suture through tissue in a direction opposite the direction of movement of the first end, and the barbs on a second portion of the first suture between a second end of the first suture and a second axial location on the first suture permitting movement of the first suture through tissue in a direction of movement of the second end and preventing movement of the first suture through tissue in a direction opposite the direction of movement of the second end, the method comprising the steps of:
   (a) inserting the first end of the first suture through skin of a patient at a first insertion point located in the NAC;
   (b) deploying the first portion of the first suture through breast tissue along a first deployment path to a first exit point located cranially of the first insertion point;
   (c) deploying the second portion of the first suture through breast tissue along a second deployment path to a second exit point located cranially of the first insertion point;
   (d) drawing the first and second portions of the first suture through the first and second exit points to elevate the NAC relative to the breast;
   (e) causing the first portion of the first suture to engage a stable anatomical feature accessible from the first exit point; and
   (f) causing the second portion of the first suture to engage a stable anatomical feature accessible from the second exit point.

2. The method of performing the cosmetic procedure of claim 1, further using a second suture including an elongated suture, and a plurality of barbs extending from the periphery of the second suture, the barbs on a first portion of the second suture between a first end of the second suture and a first axial location on the second suture for permitting movement of the second suture through the tissue in a direction of movement of the first end and preventing movement of the second suture relative to the tissue in a direction opposite the direction of movement of the first end, and the barbs on a second portion of the second suture between a second end of the second suture and a second axial location on the second suture permitting movement of the second suture through the tissue in a direction of movement of the second end and preventing movement of the second suture relative to the tissue in a direction opposite the direction of movement of the second end, wherein the method comprises:
   (a2) inserting the first end of the second suture through the skin of a patient at a first fixation point located cranially of the inframammary fold;
   (b2) causing the second suture to engage a stable anatomical feature accessible at the first fixation point;
   (c2) deploying the first portion of the second suture through breast tissue along a third deployment path from the first fixation point to a third exit point located caudally of the first fixation point;
   (d2) deploying the second portion of the second suture through breast tissue along a fourth deployment path from the first fixation point to a fourth exit point located caudally of the first fixation point; and
   (e2) manually advancing the soft tissue relative to the first portion of the second suture and the second portion of the second suture to elevate tissues of the breast towards the first fixation point.

3. The method of performing the cosmetic procedure of claim 2, further using a third suture including an elongated suture, and a plurality of barbs extending from the periphery of the suture, the barbs on a first portion of the third suture between a first end of the third suture and a first axial location on the third suture for permitting movement of the third suture through the tissue in a direction of movement of the first end and preventing movement of the third suture relative to the tissue in a direction opposite the direction of movement of the first end, and the barbs on a second portion of the third suture between a second end of the third suture and a second axial location on the third suture permitting movement of the third suture through the tissue in a direction of movement of the second end and preventing movement of the third suture relative to the tissue in a direction opposite the direction of movement of the second end, wherein the method comprises:
   (a3) inserting the first end of the third suture through the skin of a patient at a second fixation point located cranially of the inframammary fold;
   (b3) causing the third suture to engage a stable anatomical feature accessible at the second fixation point;
   (c3) deploying the first portion of the third suture through breast tissue along a fifth deployment path from the second fixation point to a fifth exit point located caudally of the second fixation point;
   (d3) deploying the second portion of the third suture through breast tissue along a sixth deployment path from the second fixation point to a sixth exit point located caudally of the second fixation point; and
   (e3) manually advancing the soft tissue relative to the first portion of the third suture and the second portion of the third suture to elevate tissues of the breast towards the second fixation point.

4. The method of claim 3, comprising performing steps (e2) and (e3) to elevate tissues of the breast towards the first fixation point and second fixation point prior to performing step (d) to elevate the NAC relative to the breast.

5. The method of claim 2, wherein the third deployment path and fourth deployment path pass through deep fibrous and fatty tissue of the breast so as to allow elevation of the breast.

6. The method of claim 2, wherein:
   step (c2) comprises deploying the first portion of the second suture through deep fibrous and fatty tissue of the breast so as to allow elevation of the breast; and
   step (d2) comprises deploying the second portion of the second suture through deep fibrous and fatty tissue of the breast so as to allow elevation of the breast;
   step (b) comprises deploying the first portion of the first suture through shallow subcutaneous tissue so as to allow elevation of the NAC towards the first and second exit points; and step (c) comprises deploying the second portion of the first suture through shallow subcutaneous tissue so as to allow elevation of the NAC towards the first and second exit points.

7. The method of claim 1, wherein:
step (e) comprises causing the first portion of the first suture to engage a fascia pectoralis; and
step (f) comprises causing the second portion of the first suture to engage a fascia pectoralis.

8. The method of claim 1, wherein step (a) comprises inserting the first end of the first suture through the skin of a patient at a first insertion point located in an areolus of the NAC.

9. The method of performing the cosmetic procedure of claim 1, wherein:
step (b) comprises deploying the first portion of the first suture through shallow subcutaneous tissue so as to allow elevation of the NAC towards the first and second exit points; and
step (c) comprises deploying the second portion of the first suture through shallow subcutaneous tissue so as to allow elevation of the NAC towards the first and second exit points.

10. The method of performing the cosmetic procedure of claim 1, wherein:
step (b) comprises deploying the first portion of the first suture to a first exit point located close to a rib; and
step (c) comprises deploying the second portion of the first suture to a second exit point located close to a rib.

11. The method of performing the cosmetic procedure of claim 1. wherein:
step (b) comprises deploying the first portion of the first suture to a first exit point located close to a second rib; and
step (c) comprises deploying the second portion of the first suture to a second exit point located close to a second rib.

12. The method of performing the cosmetic procedure of claim 1, wherein step (e) further comprises forming a surgeon's knot at the first exit point.

13. A method of performing a cosmetic procedure to reposition a nipple-areola complex (NAC) of a breast using a suture including a plurality of tissue-retainers, the tissue-retainers on a first portion of the suture between a first end of the suture and a first axial location on the suture for permitting movement of the suture through tissue in a direction of movement of the first end and preventing movement of the suture through tissue in an opposite direction, and the tissue-retainers on a second portion of the suture between a second end of the suture and a second axial location on the suture permitting movement of the suture through tissue in a direction of movement of the second end and preventing movement of the suture through tissue in an opposite direction, the method comprising steps of:
(a) inserting the first end of the suture through skin of a patient at a first insertion point located in the NAC;
(b) deploying the first portion of the suture through breast tissue along a first deployment path to a first exit point located cranially of the first insertion point;
(c) deploying the second portion of the suture through breast tissue along a second deployment path to a second exit point located cranially of the first insertion point;
(d) drawing the first and second portions of the suture through the first and second exit points to elevate the NAC relative to the breast;
(e) securing the first portion of the suture to a stable anatomical feature accessible from the first exit point; and
(f) securing the second portion of the suture to a stable anatomical feature accessible from the second exit point.

14. The method of claim 13, wherein step (a) comprises inserting the first end of the suture through the skin of a patient at a first insertion point located in an areolus of the NAC.

15. The method of claim 13, wherein:
step (b) comprises deploying the first portion of the suture through shallow subcutaneous tissue so as to allow elevation of the NAC towards the first and second exit points; and
step (c) comprises deploying the second portion of the suture through shallow subcutaneous tissue so as to allow elevation of the NAC towards the first and second exit points.

16. The method of claim 13, wherein step (b) comprises deploying the first portion of the suture through breast tissue along a first deployment path to a first exit point located cranially of the first insertion point by performing the following steps:
(b1) deploying the first portion of the suture through breast tissue along a first intermediate deployment path to an intermediate exit point located in the NAC; and
(b2) deploying the first portion of the suture through breast tissue along a second intermediate deployment path to the first exit point located cranially of the first insertion point located in the NAC.

17. A method of performing a cosmetic procedure to reposition a nipple-areola complex (NAC) of a breast using a suture including a plurality of tissue-retainers, the tissue-retainers on a first portion of the suture between a first end of the suture and a first axial location on the suture for permitting movement of the suture through tissue in a direction of movement of the first end and preventing movement of the suture through tissue in an opposite direction, and the tissue-retainers on a second portion of the suture between a second end of the suture and a second axial location on the suture permitting movement of the suture through tissue in a direction of movement of the second end and preventing movement of the suture through tissue in an opposite direction, the method comprising steps of:
(a) inserting the first end of the suture through skin of a patient at a first insertion point located in the NAC;
(b) deploying the first portion of the suture through breast tissue along a first deployment path to a first exit point located cranially of the first insertion point;
(c) deploying the second portion of the suture through breast tissue along a second deployment path to a second exit point located cranially of the first insertion point;
(d) drawing the first and second portions of the suture through the first and second exit points to elevate the NAC relative to the breast;
(e) inserting the first end of the suture through the skin of the patient at the first exit point and deploying the first portion of the suture through breast tissue to a third exit point located on the breast caudally of the first exit point; and
(f) inserting the second end of the suture through the skin of the patient at the second exit point and deploying the second portion of the suture through breast tissue to an exit point located on the breast caudally of the second exit point.

18. The method of claim 17, wherein step (a) comprises inserting the first end of the suture through the skin of a patient at a first insertion point located in an areolus of the NAC.

19. The method of performing the cosmetic procedure of claim 17, wherein:
- step (b) comprises deploying the first portion of the suture through shallow subcutaneous tissue so as to allow elevation of the NAC towards the first and second exit points; and
- step (c) comprises deploying the second portion of the suture through shallow subcutaneous tissue so as to allow elevation of the NAC towards the first and second exit points.

20. The method of performing the cosmetic procedure of claim 17, wherein step (b) comprises deploying the first portion of the suture through breast tissue along a first deployment path to a first exit point located cranially of the first insertion point by performing the following steps:
- (b1) deploying the first portion of the suture through breast tissue along a first intermediate deployment path to an intermediate exit point located in the NAC; and
- (b2) deploying the first portion of the suture through breast tissue along a second intermediate deployment path to the first exit point located cranially of the first insertion point located in the NAC.

* * * * *